(12) United States Patent
Otsuka

(10) Patent No.: US 11,191,625 B2
(45) Date of Patent: Dec. 7, 2021

(54) METHOD OF DETECTING THE POSITION OF A LATERAL CANAL EXTENDING FROM A ROOT CANAL TO A PERIODONTAL SPACE, AND DETECTING AN OPENING DIRECTION OF THE LATERAL CANAL, APPARATUS FOR THE SAME, AND A COMPUTER READABLE STORAGE MEDIUM STORING PROGRAM TO HAVE A COMPUTER EXECUTE THE METHOD

(71) Applicant: Toei Electric Co., Ltd., Tokyo (JP)

(72) Inventor: Masahiro Otsuka, Kawasaki (JP)

(73) Assignee: Toei Electric Co., Ltd.

( * ) Notice: Subject to any disclaimer, the term of this patent is extended or adjusted under 35 U.S.C. 154(b) by 93 days.

(21) Appl. No.: 15/232,961

(22) Filed: Aug. 10, 2016

(65) Prior Publication Data

US 2017/0042649 A1 Feb. 16, 2017

(30) Foreign Application Priority Data

Aug. 11, 2015 (JP) .............................. JP2015-159005

(51) Int. Cl.
*A61C 19/04* (2006.01)
*A61B 5/0534* (2021.01)
(Continued)

(52) U.S. Cl.
CPC .......... *A61C 19/042* (2013.01); *A61B 5/0534* (2013.01); *A61B 5/063* (2013.01);
(Continued)

(58) Field of Classification Search
CPC ............................ A61C 19/042; A61C 19/041
See application file for complete search history.

(56) References Cited

U.S. PATENT DOCUMENTS 6,024,565 A * 2/2000 Sicurelli .............. A61C 19/041
433/102
6,059,569 A * 5/2000 Otsuka ................. A61C 19/041
433/72

(Continued)

FOREIGN PATENT DOCUMENTS

JP WO 2004110298 A1 * 12/2004 ............. A61C 19/04
JP 2009-022726 A 2/2009
(Continued)

OTHER PUBLICATIONS

Translation of JP-2009022726-A (Year: 2009).*
(Continued)

*Primary Examiner* — Jacqueline T Johanas
*Assistant Examiner* — Stephen R Sparks
(74) *Attorney, Agent, or Firm* — Harness, Dickey & Pierce, P.L.C.

(57) ABSTRACT

A method comprising: comparing each value of measured signals with a plurality of model tooth position measurement data groups, and storing the measured signal values and an indication value at the time when a fluctuation of the indication value which indicates a distance from a root apex position to a distal end of an electrode for position detection shows an apex in a convex shape, the indication value being indicated by a model tooth position measurement data group in a predetermined relationship; and comparing second-time measured signal values and an indication value with the stored first-time measured signal values and the stored indication value, respectively, if at least two of them correspond or fall within a predetermined error range, stopping the electrode and measuring a position of the distal end of the electrode.

17 Claims, 14 Drawing Sheets

(51) Int. Cl.
  *A61B 5/00* (2006.01)
  *A61B 5/06* (2006.01)
  *A61C 5/40* (2017.01)

(52) U.S. Cl.
  CPC ............ *A61B 5/682* (2013.01); *A61B 5/7246* (2013.01); *A61B 5/742* (2013.01); *A61C 5/40* (2017.02); *A61C 19/041* (2013.01)

(56) References Cited

U.S. PATENT DOCUMENTS

| | | | | |
|---|---|---|---|---|
| 6,221,031 | B1* | 4/2001 | Heraud | A61C 19/041 600/547 |
| 7,909,604 | B2* | 3/2011 | Shoji | A61C 19/04 433/32 |
| 8,920,166 | B2* | 12/2014 | Yamashita | A61C 19/042 433/27 |
| 2008/0182223 | A1* | 7/2008 | Yamashita | A61C 19/041 433/32 |
| 2008/0280261 | A1* | 11/2008 | Shoji | A61C 19/04 433/215 |

FOREIGN PATENT DOCUMENTS

| | | | | |
|---|---|---|---|---|
| JP | 2009022726 A | * | 2/2009 | ............ A61B 5/4547 |
| JP | 2009022726 A | * | 2/2009 | ............ A61B 5/4547 |

OTHER PUBLICATIONS

First Office Action for corresponding Japan Patent Application No. 2015-159005 dated Jun. 14, 2016 (with English translation) (11 pages).

\* cited by examiner

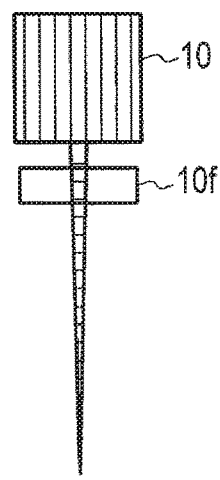
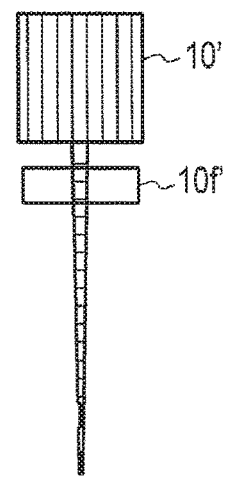
FIG. 7A     FIG. 7B
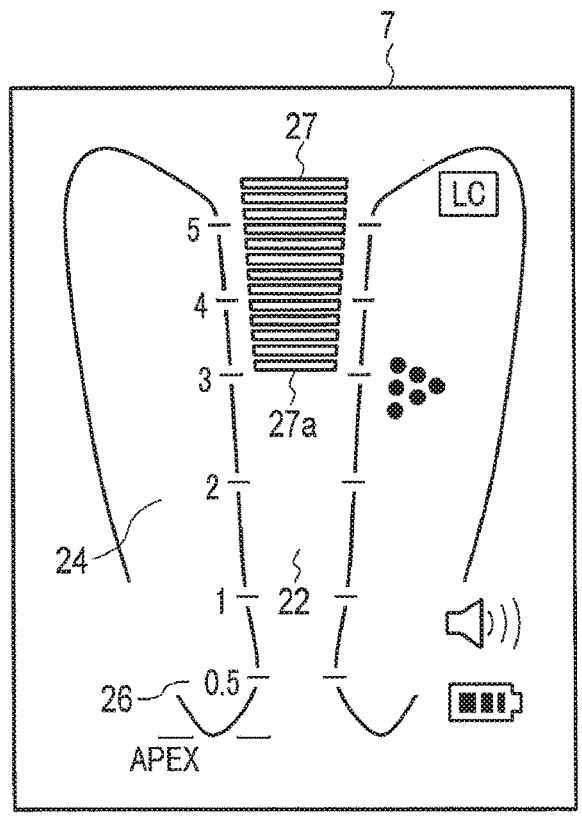
FIG. 8

METHOD OF DETECTING THE POSITION OF A LATERAL CANAL EXTENDING FROM A ROOT CANAL TO A PERIODONTAL SPACE, AND DETECTING AN OPENING DIRECTION OF THE LATERAL CANAL, APPARATUS FOR THE SAME, AND A COMPUTER READABLE STORAGE MEDIUM STORING PROGRAM TO HAVE A COMPUTER EXECUTE THE METHOD

CROSS-REFERENCE TO RELATED APPLICATION

This application is based upon and claims the benefit of priority from the prior Japanese Patent Application No. 2015-159005, filed Aug. 11, 2015, the entire contents of which are incorporated herein by reference.

BACKGROUND OF THE INVENTION

1. Field of the Invention

The present invention relates to a method of detecting a position of a lateral canal extending from a root canal (hereinafter, referred to as "lateral canal") to a periodontal space direction and detecting an opening direction of the lateral canal, an apparatus for the same, and a computer readable storage medium storing a program to have a computer execute the method, during diagnosis or treatment in dentistry. Hereinafter, "lateral canal position" refers to a position of a lateral canal in the long axis direction in a root canal, and "opening direction of lateral canal" refers to a position of a lateral canal in the rotation direction of the long axis in a root canal.

2. Description of the Related Art

When an operator treats a tooth, cases occur in which it is necessary to remove a dental pulp or a developed dentin in a root canal.

FIG. 16 is a sectional view of a tooth. In FIG. 16, reference symbol "a" denotes a tooth, "b" denotes a root canal, "c" denotes an apical foramen, "d" denotes gingiva, "e" denotes a lateral canal extending from a root canal to a periodontal space, "f" denotes an alveolar bone, "g" denotes a measurement reference point of a tooth, and "h" denotes periodontal space. After an operator measures a distance from the measurement reference point "g" of a tooth (the top of a tooth) to the apical foramen "c", he/she removes a dental pulp or the like (a nerve, a developed dentin infected with bacteria, or foreign material in a root canal) in the root canal for the measured distance. A root apex position detection apparatus is used in order to measure a distance from a measurement reference point of a tooth to a root apex. The root apex position detection apparatus is configured so that a buccal cavity electrode is disposed in a buccal cavity, a measurement electrode is inserted into a root canal, and a measurement signal is applied between the measurement electrode and the buccal cavity electrode. A root apex position is detected according to a value of a signal (a measured current In, a voltage Vn obtained by amplifying and converting In, or a DC voltage Vdc obtained by converting Vn) measured when the measurement electrode has reached the root apex position.

An operator can know a time when the measurement electrode has reached the root apex by monitoring a pointer on a display section that indicates a predetermined position.

On the other hand, when conducting treatment of a root canal, there are often times where even if an operator conducts a root canal treatment in a course of medical care, a patient's pain does not subside. When a focus of disease lies in not only a root apex but also a root side, such a case occurs that an improvement of symptoms cannot be expected unless an operator conducts treatment while being aware of a lateral canal "e".

In order to treat a lateral canal extending from a root canal to a periodontal space, it is necessary to detect the presence/absence of a lateral canal and to detect a position and an opening direction of the lateral canal.

The apparatus according to the fourth embodiment of Japan Patent Application No. 2009-22726, which is a lateral canal position detection apparatus, is configured so that a buccal cavity electrode is disposed in a buccal cavity, a measurement electrode for detecting a lateral canal position is inserted into a root canal, and at least two measurement signals (e.g., 500 Hz and 2 kHz) are applied between the measurement electrode and the buccal cavity electrode. A lateral canal position is detected based on values of at least two signals (a measured current In, a voltage Vn obtained by amplifying and converting the In, or a DC voltage Vdc obtained by converting the Vn) which are measured when the measurement electrode for detecting a lateral canal position has reached a lateral canal position. More specifically, before detecting a lateral canal position, a plurality of model tooth position measurement data groups are stored in advance. Each of the plurality of model tooth position measurement data groups comprises a plurality of sets of an indication value and a plurality of measured signals (In, Vn, or Vdc) output from the buccal cavity electrode in a state where the distal end of the measurement electrode for detecting a lateral canal position is disposed in the root canal at each of a plurality of predetermined positions in each of a plurality of model teeth. The indication value is a value indicating a distance from the position of the root apex to the distal end of the measurement electrode for detecting a lateral canal position. Respective model tooth position measurement data groups are different for respective model teeth. During the process of inserting the measurement electrode for detecting a lateral canal position into the root canal, measured signals (In, Vn, or Vdc) corresponding to signals Pn used for measurement are measured at each position at which the measurement electrode for detecting a lateral canal position is inserted. The value of each of the measured signals (In, Vn, or Vdc) is compared with each of the plurality of model tooth position measurement data groups at respective insertion positions of the measurement electrode in a root canal to output an indication value indicated by a model tooth position measurement data group in a predetermined relationship. The position of the distal end of a lateral canal position detection measurement electrode, when the fluctuation waveform of the indication value changes to show an apex in a convex shape when the measurement electrode is inserted into the root canal, is detected as a position of the lateral canal. The detected lateral canal position is displayed on the display section by distance display (data for display).

However, depending on the position of the measurement electrode in the root canal, there may be an error between the distance display shown on the display section as a result of this detection of a lateral canal position and the actual lateral canal position. The error is due to differences among the signals measured at different positions of the measurement electrode in the root canal. Accordingly, it is necessary to take new measures in order to perform the distance display for a lateral canal position more accurately.

Furthermore, the apparatus according to the fifth embodiment of Japan Patent Application No. 2009-22726 detects an opening direction of a lateral canal in two steps: (1) detecting the presence of a lateral canal and the position of the lateral canal; and (2) detecting an opening direction of the lateral canal in the root canal, using a measurement electrode for detecting a lateral canal direction.

However, if the opening direction is detected by the above-described two steps, the position of the measurement electrode for detecting a lateral canal direction in the root canal has been a cause for an error. For example, the measurement electrode for detecting a lateral canal direction vertically moves and rotates in the root canal; thus, a change in the position of the lateral canal and the opening portion of the measurement electrode for detecting a lateral canal direction in the long axis rotation direction, and a change in a measured signal value have been a cause for an error in an angle indicating the opening direction of the lateral canal. Particularly, it was difficult for an operator to rotate the measurement electrode for detecting a lateral canal direction 360 degree in one action, and to accurately detect the opening direction of the lateral canal. Thus, it is desired to detect the opening direction of the lateral canal with high accuracy by mechanically and smoothly rotating the measurement electrode for detecting a lateral canal direction in one action.

BRIEF SUMMARY OF THE INVENTION

One embodiment of the present invention was achieved to solve the above problem, and an object of one embodiment of the present invention is to detect a position of a lateral canal with higher accuracy. A further object of one embodiment of the present invention is to detect an opening direction of a lateral canal with higher accuracy.

In accordance with a first viewpoint of the present invention, a method of detecting a lateral canal position and an opening direction thereof is provided. A method of detecting a position of a lateral canal extending from a root canal to a periodontal space and an opening direction of the lateral canal, the method comprising: (1) comparing each value of first measured signals corresponding to different types of signals used for measurement corresponding to respective insertion positions of an electrode for position detection in a root canal with a plurality of model tooth root apex position measurement data groups, while the measurement-used signals are applied between the electrode for position detection and a buccal cavity electrode disposed on an inner surface of the buccal cavity, and (2) outputting a root apex position based on a result of the comparison, wherein each model tooth root apex position measurement data group consists of measurement data corresponding to measurement-used signals at respective root apex positions in each of a plurality of model teeth, and is stored in advance; (1) comparing each value of the first measured signals with a plurality of model tooth position measurement data groups, and (2) storing the first measured signal values and an indication value at the time when a fluctuation of the indication value which indicates a distance from a root apex position to a distal end of the electrode for position detection shows an apex in a convex shape, the indication value being indicated by a model tooth position measurement data group in a predetermined relationship, wherein each model tooth position measurement data group consists of a set of measurement data corresponding to measurement-used signals at respective positions in a root canal in each of a plurality of model teeth and the indication value, and is stored in advance; (1) performing lateral canal position detection once again, (2) comparing second-time first measured signal values and an indication value with the stored first-time first measured signal values and the stored indication value, respectively, (3) if at least two of them correspond or fall within a predetermined error range, stopping the electrode for position detection and measuring a position of the distal end of the electrode, and (4) outputting a result of the measurement as a position of the lateral canal; and (1) after detecting the lateral canal position, rotating a distal end of an electrode for direction detection in the long axis rotation direction at the detected lateral canal position, while different types of signals used for measurement are applied between the electrode for direction detection and the buccal cavity electrode, and (2) outputting, as an opening direction of the lateral canal, a direction of an opening of the electrode for direction detection at the time when each value of second measured signals corresponding to measurement-used signals reaches maximum, wherein the electrode for direction detection has a conductive metal portion, and an insulating film coating the surface of the conductive metal portion, and the insulating film has the opening to expose the conductive metal portion in the long axis direction of the distal end portion of the conductive metal portion.

In accordance with a second viewpoint of the present invention, an apparatus of detecting a lateral canal position and an opening direction thereof is provided. An apparatus of detecting a position of a lateral canal extending from a root canal to a periodontal space and an opening direction of the lateral canal, the apparatus comprising: an electrode for position detection; an electrode for direction detection, wherein the electrode for direction detection has a conductive metal portion and an insulating film coating the surface of the conductive metal portion, and the insulating film has an opening to expose the conductive metal portion in the long axis direction of the distal end portion of the conductive metal portion; a buccal cavity electrode disposed on an inner surface of a buccal cavity; a power source which applies different types of signals used for measurement between the electrode for position detection and the buccal cavity electrode or between the electrode for direction detection and the buccal cavity electrode; a first storage section which stores a plurality of model tooth root apex position measurement data groups and a plurality of model tooth position measurement data groups, wherein each model tooth root apex position measurement data group consists of measurement data corresponding to measurement-used signals at respective root apex positions in each of a plurality of model teeth, and each model tooth position measurement data group consists of a set of measurement data corresponding to measurement-used signals at respective positions in a root canal in each of a plurality of model teeth and an indication value which indicates a distance from a root apex position to a distal end of the electrode for position detection; a second storage section; a data processing section which comprises a root apex position detection mechanism, an electrode position detection mechanism, a lateral canal and lateral canal position detection mechanism, and a lateral canal direction detection mechanism, wherein: the root apex position detection mechanism (1) compares each value of first measured signals corresponding to measurement-used signals corresponding to respective insertion positions of the electrode for position detection in a root canal with a plurality of model tooth root apex position measurement data groups, and (2) outputs a root apex position based on a result of the comparison, the electrode position detection mechanism (1) compares each value of the first measured signals with a plurality of model tooth position measurement data groups, and (2) outputs the indication value indicated by a model tooth position measurement data group in a predetermined relationship, the lateral canal and lateral canal position detection mechanism (1) stores, in the second storage section, the first measured signal values and the indication value at the time when a fluctuation of the indication value shows an apex in a convex shape, (2) comparing, when lateral canal position detection is performed once again, second-time first measured signal values and an indication value with the stored first-time first measured signal values and the stored indication value, respectively, (3) if at least two of them correspond or fall within a predetermined error range, stops the electrode for position detection and measures a position of the distal end of the electrode, and (4) outputs a result of the measurement as a position of the lateral canal, and the lateral canal direction detection mechanism (1) rotates a distal end of the electrode for direction detection in the long axis rotation direction at the detected lateral canal position, and (2) outputs, as an opening direction of the lateral canal, a direction of the opening of the electrode for direction detection at the time when each value of second measured signals corresponding to measurement-used signals reaches maximum; and a display section which displays, selectively or entirely, data output from the data processing section.

In accordance with a third viewpoint of the present invention, a method of detecting a lateral canal position and an opening direction thereof is provided. A method of detecting a position of a lateral canal extending from a root canal to a periodontal space and an opening direction of the lateral canal, the method comprising: (1) comparing each value of first measured signals corresponding to different types of signals used for measurement corresponding to respective insertion positions of an electrode for position detection in a root canal with a plurality of model tooth root apex position measurement data groups, while the measurement-used signals are applied between the electrode for position detection and a buccal cavity electrode disposed on an inner surface of the buccal cavity, and (2) outputting a root apex position based on a result of the comparison, wherein each model tooth root apex position measurement data group consists of measurement data corresponding to measurement-used signals at respective root apex positions in each of a plurality of model teeth, and is stored in advance; (1) comparing each value of the first measured signals with a plurality of model tooth position measurement data groups, and (2) storing the first measured signal values and an indication value at the time when a fluctuation of the indication value which indicates a distance from a root apex position to a distal end of the electrode for position detection shows an apex in a convex shape, the indication value being indicated by a model tooth position measurement data group in a predetermined relationship, wherein each model tooth position measurement data group consists of a set of measurement data corresponding to measurement-used signals at respective positions in a root canal in each of a plurality of model teeth and the indication value, and is stored in advance; (1) performing lateral canal position detection once again, (2) comparing second-time first measured signal values and an indication value with the stored first-time first measured signal values and the stored indication value, respectively, (3) if at least two of them correspond or fall within a predetermined error range, stopping the electrode for position detection and measuring a position of the distal end of the electrode, and (4) outputting a result of the measurement as a position of the lateral canal; and (1) after detecting the lateral canal position, by an electrode holding mechanism provided with a holding section which holds the electrode for direction detection and a rotation mechanism which transmits rotation to the holding section, rotating a distal end of an electrode for direction detection in the long axis rotation direction at the detected lateral canal position by rotating the rotation mechanism, while different types of signals used for measurement are applied between the electrode for direction detection and the buccal cavity electrode, and (2) outputting, as an opening direction of the lateral canal, a direction of an opening of the electrode for direction detection at the time when each value of second measured signals corresponding to measurement-used signals reaches maximum, wherein the electrode for direction detection has a conductive metal portion, and an insulating film coating the surface of the conductive metal portion, and the insulating film has the opening to expose the conductive metal portion in the long axis direction of the distal end portion of the conductive metal portion.

In accordance with a fourth viewpoint of the present invention, an apparatus of detecting a lateral canal position and an opening direction thereof is provided. An apparatus of detecting a position of a lateral canal extending from a root canal to a periodontal space and an opening direction of the lateral canal, the apparatus comprising: an electrode for position detection; an electrode for direction detection, wherein the electrode for direction detection has a conductive metal portion and an insulating film coating the surface of the conductive metal portion, and the insulating film has an opening to expose the conductive metal portion in the long axis direction of the distal end portion of the conductive metal portion; a buccal cavity electrode disposed on an inner surface of a buccal cavity; a power source which applies different types of signals used for measurement between the electrode for position detection and the buccal cavity electrode or between the electrode for direction detection and the buccal cavity electrode; a first storage section which stores a plurality of model tooth root apex position measurement data groups and a plurality of model tooth position measurement data groups, wherein each model tooth root apex position measurement data group consists of measurement data corresponding to measurement-used signals at respective root apex positions in each of a plurality of model teeth, and each model tooth position measurement data group consists of a set of measurement data corresponding to measurement-used signals at respective positions in a root canal in each of a plurality of model teeth and an indication value which indicates a distance from a root apex position to a distal end of the electrode for position detection; a second storage section; a data processing section which comprises a root apex position detection mechanism, an electrode position detection mechanism, a lateral canal and lateral canal position detection mechanism, and a lateral canal direction detection mechanism, wherein: the root apex position detection mechanism (1) compares each value of first measured signals corresponding to measurement-used signals corresponding to respective insertion positions of the electrode for position detection in a root canal with a plurality of model tooth root apex position measurement data groups, and (2) outputs a root apex position based on a result of the comparison, the electrode position detection mechanism (1) compares each value of the first measured signals with a plurality of model tooth position measurement data groups, and (2) outputs the indication value indicated by a model tooth position measurement data group in a predetermined relationship, the lateral canal and lateral canal position detection mechanism (1) stores, in the second storage section, the first measured signal values and the indication value at the time when a fluctuation of the indication value shows an apex in a convex shape, (2) comparing, when lateral canal position detection is performed once again, second-time first measured signal values and an indication value with the stored first-time first measured signal values and the stored indication value, respectively, (3) if at least two of them correspond or fall within a predetermined error range, stops the electrode for position detection and measures a position of the distal end of the electrode, and (4) outputs a result of the measurement as a position of the lateral canal, and the lateral canal direction detection mechanism (1) rotates a distal end of the electrode for direction detection in the long axis rotation direction at the detected lateral canal position by rotating the rotation mechanism by the electrode holding mechanism, and (2) outputs, as an opening direction of the lateral canal, a direction of the opening of the electrode for direction detection at the time when each value of second measured signals corresponding to measurement-used signals reaches maximum; and a display section which displays, selectively or entirely, data output from the data processing section.

According to one embodiment of the present invention, it is possible to detect a position of a lateral canal with higher accuracy. Additionally, according to one embodiment of the present invention, it is possible to detect an opening direction of a lateral canal with higher accuracy.

BRIEF DESCRIPTION OF THE DRAWINGS

The accompanying drawings, which are incorporated in and constitute apart of the specification, illustrate embodiments of the invention, and together with the general description given above and the detailed description of the embodiments given below, serve to explain the principles of the invention.

FIGS. 7A and B are sectional views of the measurement electrode comprising a stopper according to one embodiment of the present invention.

FIG. 8 is a diagram showing an example of a display section according to one embodiment of the present invention.

DETAILED DESCRIPTION OF THE INVENTION

Figure 1:
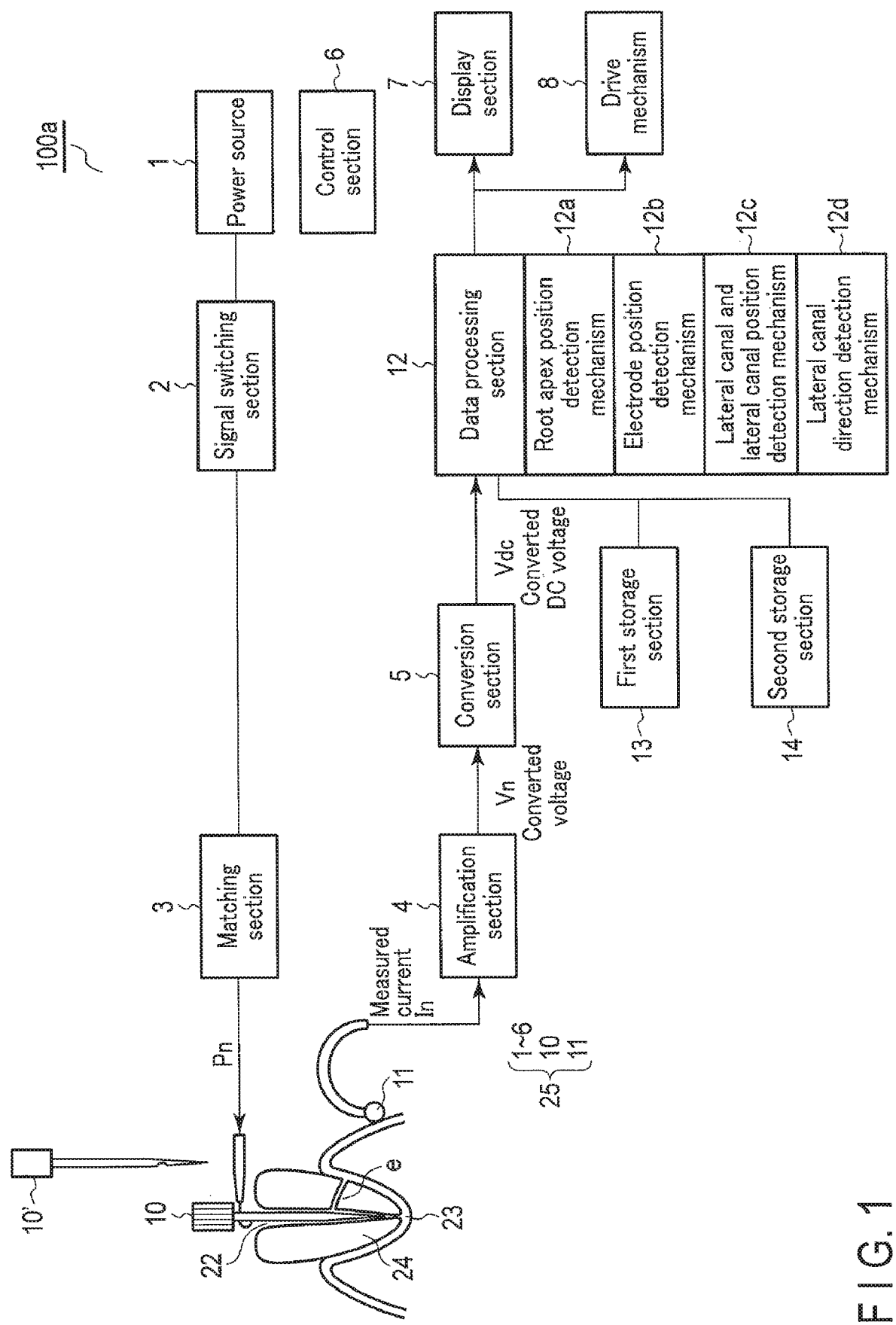
FIG. 1 is a block diagram showing a circuit of an apparatus for detecting a position of a lateral canal and an opening direction thereof (hereinafter, referred to as "lateral canal detection apparatus") according to one embodiment of the present invention.

FIG. 1 shows a first embodiment of the lateral canal detection apparatus 100a according to the present invention.

In FIG. 1, reference numeral 1 denotes a power source which outputs signals Pn used for measurement having one or a plurality of different frequencies. The power source 1 outputs signals Pn used for measurement at two frequencies, for example, 500 Hz and 2 kHz. Reference numeral 2 denotes a signal switching section, which selects either one of signals Pn of 500 Hz or 2 kHz, or performs switching between the signals to sequentially feed signals to a matching section 3 according to an instruction from a control section 6. The matching section 3 converts the signals Pn to be fed to the measurement electrode 10 for detecting a root apex position and a lateral canal position (hereinafter, referred to as "electrode for position detection") into voltages suitable for measurement, and feeds them to an amplification section 4. The amplification section 4 converts and amplifies measured currents In fed from a buccal cavity electrode 11 disposed on the gingiva of a subject tooth 24 into measured voltages Vn. Reference numeral 5 denotes a conversion section, which converts a measured voltage Vn into a DC voltage Vdc. Reference numeral 6 denotes a control section 6, which governs control of respective elements in the lateral canal detection apparatus 100a to conduct processing. Reference numeral 7 denotes a display section, which displays a measurement result based upon a DC voltage Vdc according to an instruction from the control section and/or generates an alarm sound. The display section 7 can display, selectively or entirely, the data output from the data processing section 12. Reference numeral 8 denotes a drive mechanism for automatically moving the electrode 10 for position detection toward a root apex position 23 when the lateral canal detection apparatus 100a is automated, and the drive mechanism can be provided with an interface circuit. The drive mechanism can be adopted if necessary. Reference numeral 12 denotes a data processing section which processes a DC voltage Vdc to prepare display data which is transmitted to the display section 7. When signals Pn used for measurement at a frequency of, for example, 500 Hz or 2 kHz are applied from the power source 1 to the electrode 10 for position detection (e.g., a reamer), two kinds of measured currents at respective frequencies ($In_{500\ Hz}$ and $In_{2kHz}$) are detected between the electrode 10 and the buccal cavity electrode 11. Those two kinds of measured currents are sequentially detected by the detection section 25 in correspondence to the insertion position of the electrode 10 as the process of inserting the electrode (reamer) 10 into the root canal 22 toward the root apex position 23 progresses.

In FIG. 1, reference numeral 10' denotes a measurement electrode for detecting a lateral canal direction (hereinafter, referred to as "electrode for direction detection") used instead of the electrode 10 for position detection, after using the electrode 10 to detect a lateral canal position. Reference numeral 12a denotes a root apex position detection mechanism which detects a position of a root apex. Reference numeral 12b denotes an electrode position detection mechanism which detects a position of a distal end of the electrode 10 for position detection. Reference numeral 12c denotes a lateral canal and lateral canal position detection mechanism which detects a lateral canal's presence/absence and a position of the lateral canal. Reference numeral 12d denotes a lateral canal direction detection mechanism which detects an opening direction of a lateral canal. The data processing section 12 can selectively switch among those detection mechanisms 12a to 12d. A switching mechanism may be provided in the data processing section 12 to switch among those detection mechanisms 12a to 12d. Reference numeral 13 denotes a first storage section which stores a plurality of model tooth root apex position measurement data groups and a plurality of model tooth position measurement data groups. Each of the plurality of model tooth root apex position measurement data groups comprises a plurality of measured signals (In, Vn which is obtained by amplifying and converting the In, or Vdc which is obtained by converting the Vn) fed from the buccal cavity electrode in a state where the distal end of the electrode 10 for position detection is disposed at the root apex position of each model tooth. Each of the plurality of model tooth position measurement data groups comprises a plurality of sets consisting of a plurality of measured signals (In, Vn, or Vdc) fed from the buccal cavity electrode, and an indication value which indicates a distance from the root apex position to the distal end of the electrode 10 in a state where the distal end of the electrode 10 is disposed at each of a plurality of predetermined positions in the root canal of each model tooth. Each model tooth position measurement data group is different for each model tooth. Each of the model tooth position measurement data groups is measurement data of each of model teeth having a root apex but no lateral canal. The plurality of model tooth apex root position measurement data groups and a plurality of model tooth position measurement data groups are stored in advance in the first storage section 13 prior to the detection of a lateral canal position. Reference numeral 14 is a second storage section which stores a plurality of measured signals (In, Vn, or Vdc) which change as the electrode 10 is inserted into the root canal, and an indication value, at the time when the indication value, which indicates a distance from the root apex position to the distal end of the electrode 10, shows an apex. The details of the second storage section 14 will be described later.

The apparatus shown in FIG. 1 is provided with a function of detecting a root apex position using the electrode 10 for position detection, a function of detecting a position of the distal end of the electrode 10, a function of detecting an existence/absence of a lateral canal and a position of the lateral canal, and a function of detecting an opening direction of a lateral canal using electrode 10' for direction detection. Each of the functions will be described below.

In FIG. 1, during the process of inserting the distal end of the electrode 10 for position detection into the root canal 22, the power source 1 alternatively and sequentially applies the signals $Pn_{500\ Hz}$ and $Pn_{2kHz}$ between the electrode 10 and the buccal cavity electrode 11. As a result, as the distal end of the electrode 10 for position detection is being inserted into the root canal 22, the plurality of measured currents obtained from the buccal cavity electrode 11 change. The plurality of measured currents are sequentially detected by the detection section 25.

The function of detecting a root apex position in FIG. 1, etc. is described below. The data processing section 12 is provided with a root apex position detection mechanism 12a. The root apex position detection mechanism 12a compares a plurality of measured currents In detected by the detection section 25 (or Vn obtained by amplifying and converting the In, or Vdc obtained by converting the Vn) with the plurality of model tooth apex position measurement data groups stored in the first storage section 13. Then, a plurality of model tooth apex position measurement data groups in a predetermined relationship (e.g., a corresponding relationship), are detected. The correspondence in the result of comparison means that the distal end of the electrode 10 for position detection is located at the root apex; accordingly, at this time, the root apex position can be output based on the moving distance of the electrode 10 from the top of the tooth, and the display section 7 can display the root apex position.

Figure 2:
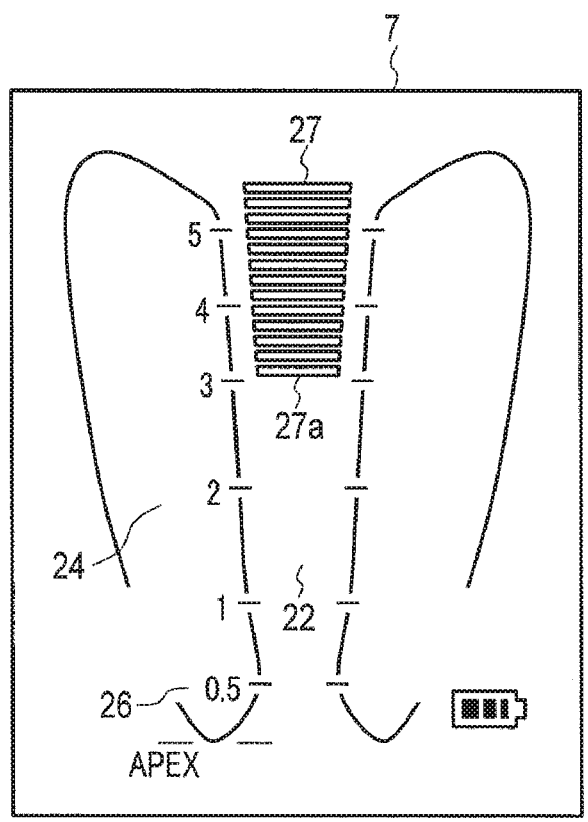
FIG. 2 is a diagram showing an example of a display section according to one embodiment of the present invention.

The function of detecting the position of the distal end of the electrode 10 for position detection according to FIG. 1, etc. is described below. The data processing section 12 is provided with an electrode position detecting mechanism 12b. The electrode position detection mechanism 12b compares the plurality of measured currents In detected by the detection section 25 (or Vn obtained by amplifying and converting the In, or Vdc obtained by converting the Vn) with the plurality of model tooth position measurement data groups at respective measurement positions in the root canal, which are stored in the first storage section 13. Then, an indication value is output, which indicates a distance from a root apex position to the distal end of the electrode for position detection, indicated by a model tooth position measurement data group in a predetermined relationship. The display section 7 can display the position of the distal end of the electrode 10 for position detection based on the indication value which indicates a distance from the root apex position to the distal end of the electrode 10. An example of the display section 7 is shown in FIG. 2. The operator can accurately know the status of the electrode 10 for position detection as the distal end gets close to the root apex position 23 by observing the display. The display section 7 can display the display data for displaying fluctuation waveforms of the plurality of measured signals (In, Vn, or Vdc) and the indication values.

Thus, the apparatus shown in FIG. 1 can detect, at a distance of every 1 mm, for example, from the root apex position, the status of the electrode 10 for position detection as the distal end gets close to the root apex position 23 in 1 mm units by generating a model tooth position measurement data group of the model tooth 24'.

The detected position of the distal end of the electrode 10 for position detection can be displayed by the display section 7 shown in FIG. 2. The display section 7 in FIG. 2 shows the subject tooth 24 and the root canal 22. A scale is drawn on the subject tooth 24 to indicate a distance 26 from the root apex position. A horizontal stripe display 27 is drawn at the root canal part. As the electrode 10 for position detection is being inserted toward the root apex position, the lowest portion 27a of the horizontal stripe display descends and displays the distal end position of the electrode 10. FIG. 2 shows that the distal end of the electrode 10 is located 3 mm before the root apex position.

In a case where an automatic insertion apparatus for automatically inserting the electrode 10 is adopted, a mechanism for detecting how far the electrode 10 is automatically inserted can be incorporated into such an automatic insertion apparatus, as a mechanism for measuring the position of the distal end of the electrode 10 for the position detection in the root canal.

Figure 3:
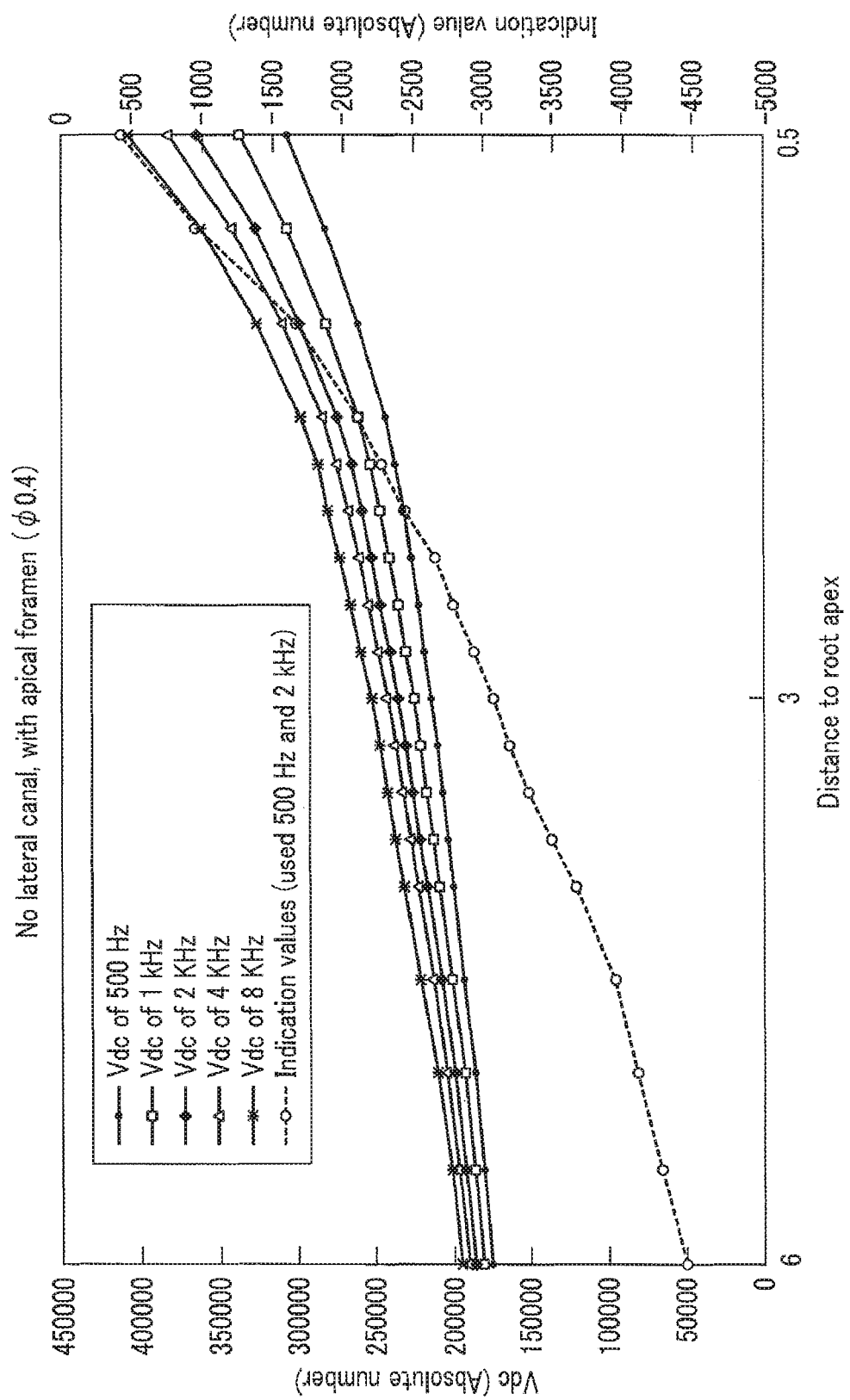
FIG. 3 is a diagram showing fluctuation waveforms of DC voltages obtained by converting measured currents of respective measurement frequencies and indication values that indicate a position of the distal end of a measurement electrode for position detection of a subject tooth which does not have a lateral canal, but has an apical foramen using the apparatus shown in FIG. 1.

The function of detecting a lateral canal's presence/absence and the position of the lateral canal according to FIG. 1, etc. is described below. The data processing section 12 is provided with a lateral canal and lateral canal position detection mechanism 12c. FIG. 3 shows the result of examination of a subject tooth having an apical foramen, but no lateral canal, using the apparatus shown in FIG. 1. Herein, voltages at each frequency of 500 Hz, 1 kHz, 2 kHz, 4 kHz, and 8 kHz were used as signals Pn used for measurement. In FIG. 3, fluctuation waveforms of the DC voltages obtained by converting the measured currents at each measurement frequency, and a fluctuation waveform of the indication value detected by the electrode position detection mechanism 12b, are shown when the electrode 10 for position detection is inserted into the root canal. The indication values of the plurality of model tooth position measurement data groups which have a predetermined relationship with the plurality of measured signals (In, Vn, or Vdc) can be expressed by, for example, the values indicated in the vertical axis shown in FIG. 3. In FIG. 3, the fluctuation waveform of the indication value for the subject tooth having no lateral canal increases steadily.

Figure 4:
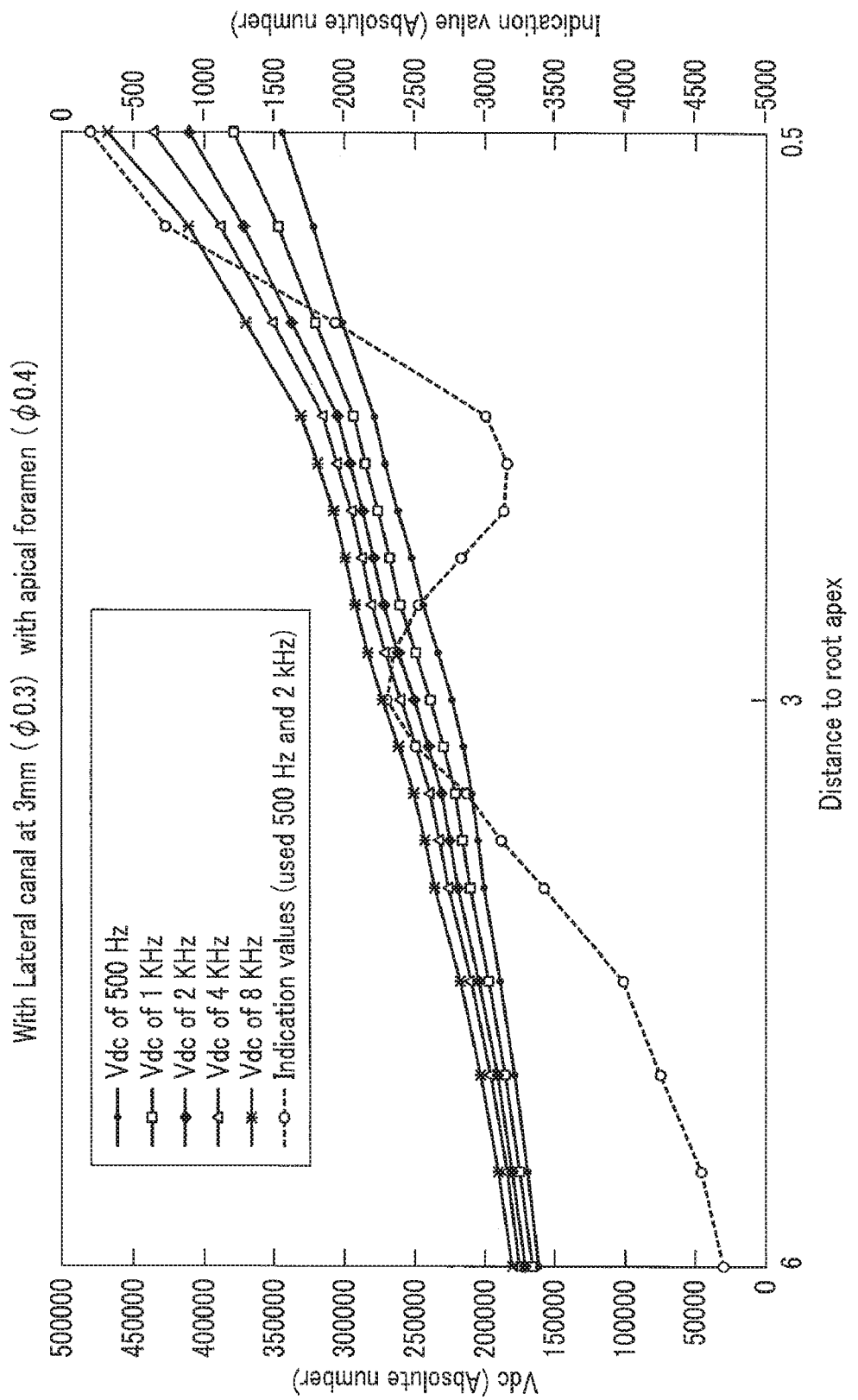
FIG. 4 is a diagram showing fluctuation waveforms of DC voltages obtained by converting measured currents of respective measurement frequencies, and indication values indicating a position of the distal end of a measurement electrode for position detection of a subject tooth which has a lateral canal and an apical foramen using the apparatus shown in FIG. 1.

On the other hand, FIG. 4, using the same apparatus as the one shown in FIG. 1, shows a result of examining the subject tooth 24 having a lateral canal positioned around 3 mm from the root apex and having an apical foramen. The frequencies of the signals Pn are 500 Hz, 1 kHz, 2 kHz, 4 kHz, and 8 kHz. FIG. 4 also shows fluctuation waveforms of DC voltages obtained by converting the measured currents at each measurement frequency, and a fluctuation waveform of the indication value detected by the electrode position detection mechanism 12b at the time of inserting the electrode for position detection into the root canal.

The fluctuation waveform of the indication value in FIG. 4, i.e., the waveform indicated by "--o--", is that of the indication value obtained from a plurality of model tooth position measurement data groups using the DC voltages $Vdc_{500\ Hz}$ and $Vdc_{2\ kHz}$ corresponding to signals used for measurement at two frequencies, 500 Hz and 2 kHz.

The fluctuation waveform of an indication value in FIG. 4 shows an apex in a convex shape at the scale of around 3 mm. As shown in FIG. 4, in the subject tooth having an apical foramen, the fluctuation waveforms of the DC voltages Vdc, which correspond to the signals Pn used for measurement at each frequency of 500 Hz, 1 kHz, 2 kHz, 4 kHz, and 8 kHz, steadily increase, similar to the waveforms of the DC voltages Vdc shown in FIG. 3 for the case where the subject tooth has no lateral canal; thus, it is not easy to detect a lateral canal from the fluctuation waveforms of the DC voltages Vdc shown in FIG. 3 and FIG. 4.

Figure 5:
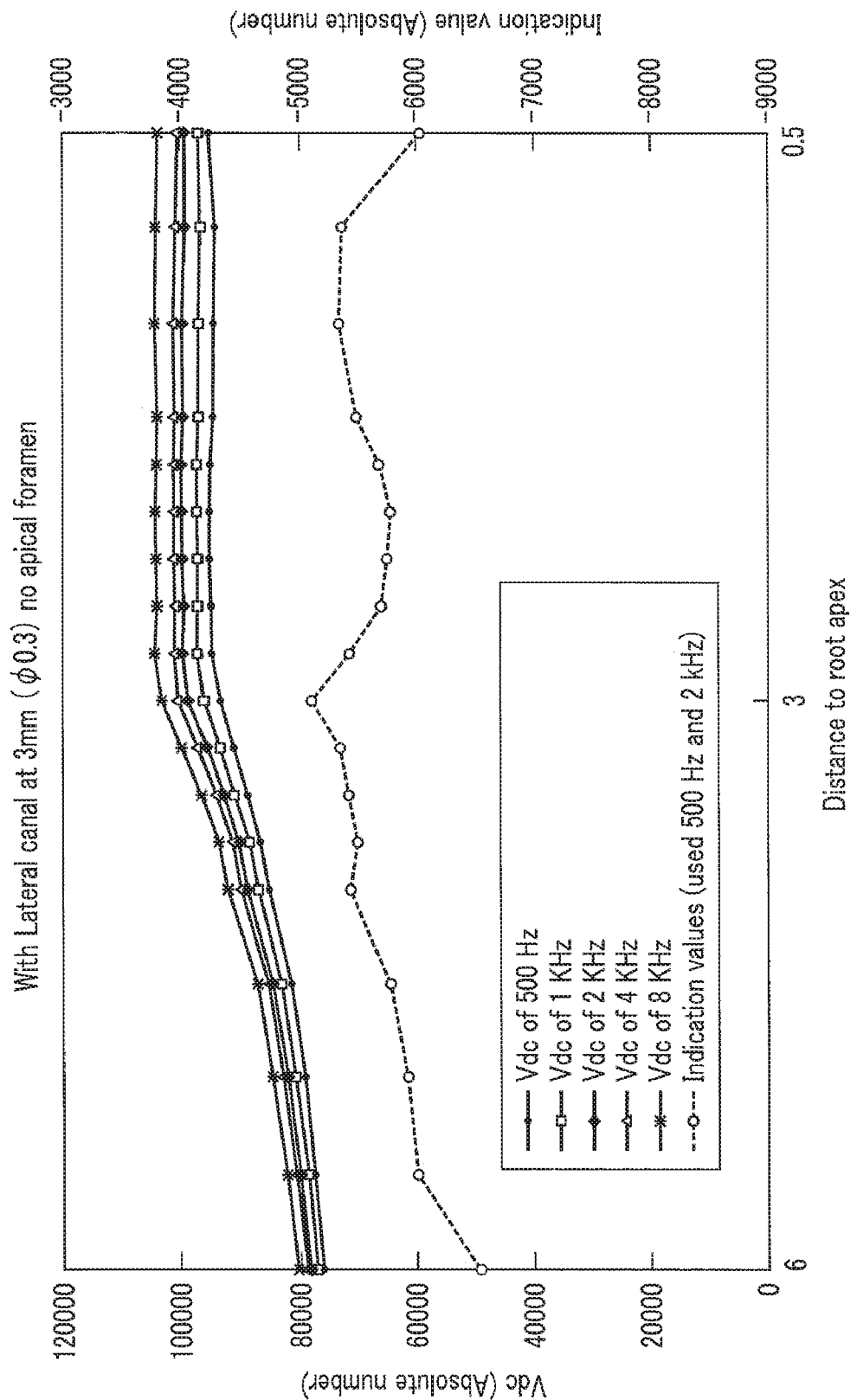
FIG. 5 is a diagram showing fluctuation waveforms of DC voltages obtained by converting measured currents of respective measurement frequencies, and indication values indicating a position of the distal end of a measurement electrode for position detection of a subject tooth which has a lateral canal but does not have an apical foramen using the apparatus shown in FIG. 1.

FIG. 5 shows a result of examination of the subject tooth 24 having a lateral canal positioned around 3 mm from the root apex and having no apical foramen, using the same apparatus as the one shown in FIG. 1. The frequencies of the signals Pn are 500 Hz, 1 kHz, 2 kHz, 4 kHz, and 8 kHz. FIG. 5 also shows fluctuation waveforms of DC voltages obtained by converting the measured currents at each measurement frequency, and a fluctuation waveform of the indication value detected by the electrode position detection mechanism 12b at the time of inserting the electrode for position detection into the root canal.

Note the fluctuation waveform of each DC voltage Vdc in FIG. 5. In FIG. 1, when the electrode 10 for position detection is inserted into the root canal toward the root apex position 23, the current flowing between the electrode 10 and the buccal cavity electrode 11 flows from the electrode up to the position where the lateral canal is via a lateral canal. In other words, a current flows in accordance with a distance between the distal end of the electrode 10 and a lateral canal. However, it can be assumed that a distance between the body surface of the conductive electrode and the lateral canal becomes constant after the electrode 10 passes the lateral canal position, and the current flowing via the lateral canal will be at approximately a constant value in accordance with the same distance.

Note the fluctuation waveforms of the indication value in FIGS. 3, 4, and 5. In FIG. 3, the fluctuation waveform of the indication value for the subject tooth having no lateral canal increases steadily; on the other hand, in each of FIGS. 4 and 5, the fluctuation waveform of the indication value for the subject tooth having a lateral canal shows an apex in a convex shape. It is possible to accurately and easily detect whether or not the subject tooth has a lateral canal by detecting the fluctuation waveforms having a convex-shaped change.

The reason why the indication values in FIGS. 3 and 4 are different is because the change that will be described below is observed in the measured current In in FIG. 4. In FIG. 1, the current flowing between the electrode 10 for position detection and the buccal cavity electrode 11 flows from the electrode up to the position where the lateral canal is via the root apex and the lateral canal when the electrode 10 is inserted into the root canal 22 toward the root apex position 23. In other words, a current flows in accordance with a distance between the distal end of the electrode 10 and a lateral canal. However, it can be assumed that a distance between the body surface of the conductive electrode and the lateral canal becomes constant after the electrode 10 passes the lateral canal position, and the current flowing via the lateral canal will be at approximately a constant value in accordance with the same distance. The above-described difference in the indication values in FIGS. 3 and 4 is caused by a change such as this in the measured current in the case of FIG. 4.

Furthermore, the data indicating a distance from the root apex position to the distal end of the electrode for position detection is adopted as the indication value for the apparatus shown in FIG. 1. Thus, the position where the fluctuation waveform of the indication value shows an apex in a convex shape on the X axis can be detected as a position where the lateral canal is by the lateral canal and lateral canal position detection mechanism 12c.

Figure 6:
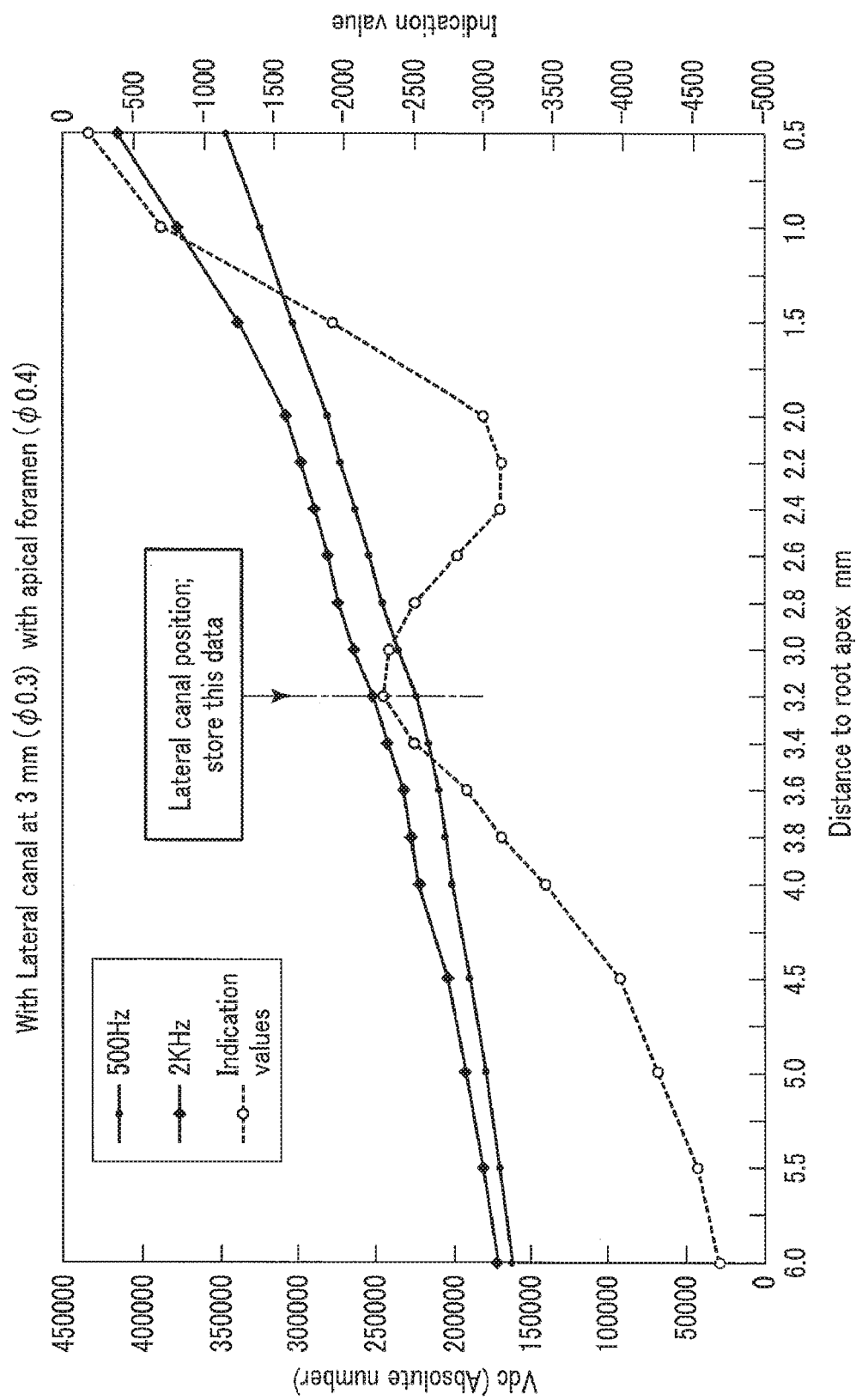
FIG. 6 is a diagram showing fluctuation waveforms of DC voltages obtained by converting measured currents of respective measurement frequencies, and indication values indicating a position of the distal end of a measurement electrode for position detection of a subject tooth which has a lateral canal and an apical foramen using the apparatus shown in FIG. 1.

FIG. 6 shows the result of examination shown in FIG. 4 only for the DC voltages at the frequencies of 500 Hz and 2 kHz obtained by converting the measured currents corresponding to the signals Pn used for measurement. An apex in a convex shape found on the fluctuation waveform of the indication value shows that the lateral canal exists at the distance of 3.0 mm to the root apex. The plurality of measured signal values (In, Vn, or Vdc) and the indication value at this time are stored in the second storage section 14 as first-time measured signal values (In, Vn, or Vdc) and the indication value. The values of the plurality of measured signals stored in the second storage section 14 may be any of In, Vn, and Vdc.

Next, the electrode 10 for position detection is once again inserted into the root canal. During the process of inserting the electrode 10 for position detection into the root canal, the second-time measured signal values (In, Vn, or Vdc) and indication values are respectively and consecutively compared with the first-time measured signal values (In, Vn, or Vdc) and the indication value stored in the second storage section 14. When, as a result of the comparison, at least two of the measured signals (In, Vn, or Vdc) and the indication value match or fall within a predetermined error range, it can be determined that the distal end of the electrode 10 for position detection reaches the lateral canal position. The distal end of the electrode 10 reaching the lateral canal position can be displayed to the operator. When, as a result of the comparison, at least two of the measured signals (In, Vn, or Vdc) and the indication value match or fall within a predetermined error range, the electrode 10 can be stopped, and the position of the distal end of the electrode 10 for position detection is measured to be output as a lateral canal position. The display may be notified by an alarm or vibration. It is also possible to notify the operator of the display by flashing the distance display. The notification can be automated. The predetermined error range herein is an error of a few percent, for example.

Even a slight displacement of the position of the electrode 10 for position detection in the root canal causes a change in the values of the measured currents In corresponding to each of the signals used for measurement; as a result, the fluctuation waveform of the indication value shown in FIG. 6 will also be changed. For this reason, there will be an error between the distance display on the display section when the fluctuation waveform of the indication value shows an apex in a convex shape and the actual position of the lateral canal. Accordingly, in order to perform the distance display for the lateral canal position with higher accuracy, the above-described lateral canal position detection is performed once again. The lateral canal position detection is performed using not only the indication values, but also the measured signal values. The reason for using the values of the measured signal values as well as the indication values is as follows. FIG. 6 shows a point (where the horizontal axis is marked as around 1.6 mm) having a same value as the indication value at the apex in the fluctuation waveform of the indication value (the point where the horizontal axis "distance to the root apex" is marked as around 3.0 mm). For this reason, when the lateral canal position detection is performed once again, the lateral canal position cannot be specified only by the consecutive comparison of the second-time indication value with the first-time indication value. On the other hand, the DC voltages Vdc corresponding to the signals used for measurement are different for the apex in the fluctuation waveform of the indication value and the other point having the same value as the apex point in FIG. 6. Accordingly, the lateral canal position can be specified using not only the indication values, but also the values of the measured signals.

The lateral canal position detection is once again performed, and the second-time measured signal values and the indication value are respectively compared with the stored first-time measured signal values and the stored indication value. When, as a result of the comparison, the measured signal values (In, Vn, or Vdc) and the indication value match or fall within a predetermined error range, the electrode for position detection is stopped and the position of the distal end of the electrode is measured to be output as the lateral canal position. The output lateral canal position is displayed on the display section in the form of distance display. As described above, the DC voltages Vdc corresponding to the signals used for measurement are different for the apex in the fluctuation waveform of the indication value and the other point having the same value as the apex point in FIG. 6. Thus, it is possible to perform the distance display for the lateral canal position with higher accuracy by measuring the distal end position of the electrode 10 for position detection when at least two values match or fall within a predetermined error range.

The apparatus shown in FIG. 1 may further be provided with a measurement mechanism for automatically measuring the distal end position of the electrode 10 when the first-time measured signal values and the indication value and the second-time measured signal values and the indication value match or fall within a predetermined error range as a result of comparing those values.

The electrode 10 for position detection may be provided with a stopper 10f for fixing the electrode to a subject tooth, like the one shown in FIG. 7A. For example, when the distal end of the electrode 10 for position detection has reached the lateral canal position, the electrode 10 is stopped, and the stopper 10f is brought down to the top of the subject tooth to fix the electrode 10. After fixing the electrode 10, the distance from the distal end of the electrode 10 to the stopper 10f is measured. The apparatus shown in FIG. 1 may be provided with such a measurement mechanism. Such a mechanism enables the apparatus to detect a lateral canal position with higher accuracy.

The stopper 10f may be of the size which allows the stopper 10f to fix the electrode 10 to a subject tooth, and it may be smaller than a subject tooth. In order to measure the distance from the distal end of the electrode 10 to the stopper 10f, the electrode 10 may be graduated, or multi-colored.

The data processing section 12 may be provided with a mechanism for automatically measuring a distance from the distal end of the electrode 10 to the stopper 10f by automatically moving the stopper 10f. This automatic measurement mechanism can inform the operator of the lateral canal position through the display on the display section 7.

The case where the display section 7 shown in FIG. 8 is used is explained. As when inserting the electrode 10 for position detection into the root canal of the subject tooth, the lowest portion 27a of the horizontal stripe display 27 also descends toward the root apex position 23, however, the lowest portion 27a is reversed at the lateral canal position to ascend. The presence of the lateral canal can be detected by this reversal. Furthermore, this reversal position can be detected as the position where the lateral canal is present. The display section 7 can display, selectively or entirely, the detected lateral canal position and display data for displaying fluctuation waveforms of the plurality of measured signals (In, Vn, or Vdc) and the indication values.

The function of detecting an opening direction of a lateral canal according to FIG. 1, etc. is described below. The data processing section 12 is provided with a lateral canal direction detection mechanism 12d. The apparatus shown in FIG. 1 is further provided with an electrode 10' for direction detection which is replaceable with the electrode 10 for position detection. Refer to FIGS. 9A to D. The electrode 10' for direction detection as shown in FIGS. 9A to D is prepared. In the electrode 10' for direction detection, as shown in FIG. 9B, an insulating film 10b is applied at least to the surface of a pin-shaped conductive metal portion 10a to be inserted into the root canal to coat the surface. As shown in FIGS. 9B and C, an opening 10c is provided to expose a part of the conductive metal portion 10a in the long axis direction of at least the distal end portion of an insulating film 10b. The metal portion 10a is electrically coupled to the external environment of the insulating film 10b via the opening 10c. The opening 10c does not consist of the distal end of the metal portion 10a only; it has a certain size so that the metal portion can be electrically coupled to the external environment of the insulating film 10b via the opening 10c.

Figure 9A:
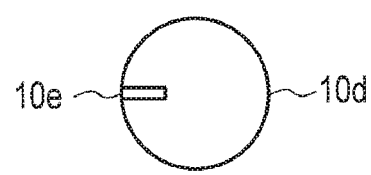
FIGS. 9A to D are sectional views of the measurement electrode for direction detection according to one embodiment of the present invention.

As shown in FIG. 9A, a marking 10e is indicated on a handle 10d of the electrode 10' for direction detection. The marking 10e is arranged in the same direction as the opening 10e when the handle 10d is viewed from above.

In the following, the procedure of arranging the electrode 10' for direction detection at the lateral canal position is described.

The operator examines the subject tooth 24 having a lateral canal so that he/she can check the presence of the lateral canal in the subject tooth 24 through, for example, the display of "LC" (Lateral Canal) on the display section 7 as shown in FIG. 8, and the lateral canal position through the distance display.

The distance display can indicate the position of the lateral canal by dots (six dots in FIG. 8) if there is a lateral canal 3 mm before the root apex. The distance display corresponds to the value (3.0) in the center of the display. Thus, the distal end of the electrode 10' for direction detection can be arranged at the lateral canal position by inserting the electrode 10' into the root canal up to the position where the horizontal stripe display indicates the value 3.0.

The electrode 10' for direction detection may be provided with a stopper 10f for fixing the electrode to a subject tooth, like the one shown in FIG. 7B. For example, if the electrode 10 for position detection is provided with a stopper 10f, a distance from the distal end of the electrode 10 to the stopper 10f is first measured with the above-described method in order to detect the lateral canal position. Next, the electrode 10 for position detection is replaced with the electrode 10' for direction detection. Then, after setting the position of the stopper 10f of the electrode 10' for direction detection based on the detected lateral canal position, the electrode 10' for direction detection is arranged at a position where the stopper 10f is in contact with the top of the subject tooth while the electrode 10' for direction detection is being inserted into the root canal. By this procedure, the distal end of the electrode 10' for direction detection can be arranged at the lateral canal position. Thus, the opening direction of the lateral canal can be detected with higher accuracy. Herein, the top of the subject tooth refers to the measurement reference point "g" of a tooth.

The stopper 10f may be of the size which allows the stopper 10f to fix the electrode 10' for direction detection to a subject tooth, and it may be smaller than a subject tooth. In order to set the position of the stopper 10f, the electrode 10' may be graduated, or multi-colored.

The data processing section 12 may also be provided with a setting mechanism for setting the position of the stopper 10f based on the detected lateral canal position by automatically moving the stopper 10f. The data processing section 12 may further be provided with an arrangement mechanism for arranging the electrode 10' for direction detection by automatically moving the electrode 10' at a position where the stopper 10f is in contact with the top of the subject tooth when inserting the electrode 10' for direction detection into the root canal.

The electrode 10' for direction detection is arranged at the lateral canal position detected with the above-described procedure. At this position, the power source 1 sequentially applies different signals Pn used for measurement to one of the electrode 10' for direction detection and the buccal cavity electrode 11 by switching between the signals, and the distal end of the electrode 10' is rotated in the long axis rotation direction in the root canal. The detection section 25 sequentially detects measured currents corresponding to the signals Pn between the electrode 10' and the buccal cavity electrode 11 during the process of rotating the electrode 10' in the long axis rotation direction at the detected lateral canal position. When the electrode 10' is rotated at this position and the opening 10c of the insulating film 10b matches the opening of the lateral canal, the measured current In flowing between the electrode 10' and the buccal cavity electrode 11 increases. On the other hand, when the electrode 10' is rotated and the opening 10c of the insulating film 10b is misaligned from the opening of the lateral canal, the measured current In flowing between the electrode 10' and the buccal cavity electrode 11 decreases. The reason for the above phenomenon is a decrease of measured current In flowing via the lateral canal due to a longer distance between the opening 10c and the opening of the lateral canal when the misalignment of the opening 10c from the opening of the lateral canal occurs since measured current In flows via the apical foramen and the lateral canal. The lateral canal direction detection mechanism 12d can detect the direction of the opening 10c, as the opening direction of the lateral canal, at the time when the current, which changes as the electrode 10' is rotated at the detected lateral canal position, becomes maximum.

Figure 10:
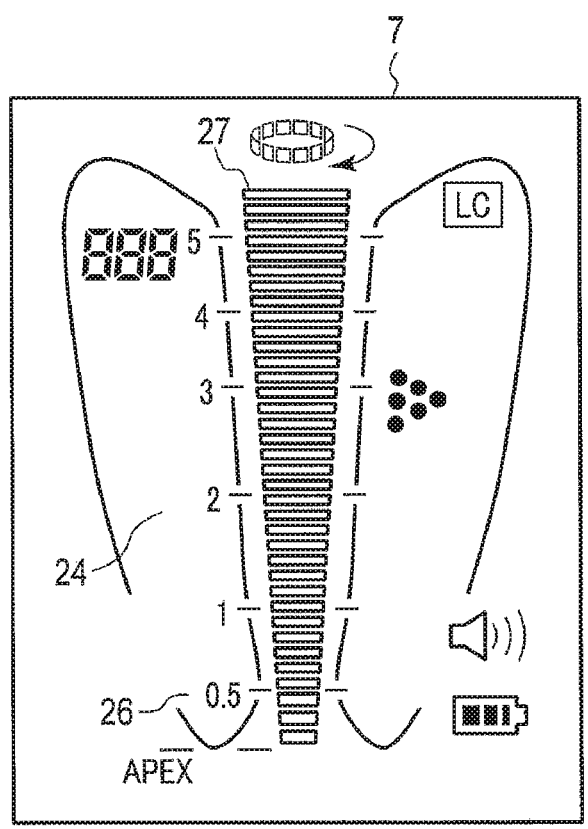
FIG. 10 is a diagram showing an example of a display section according to one embodiment of the present invention.

FIG. 10 is an example of the display on the display section 7 when the lateral canal direction is detected. The presence of a lateral canal is indicated by "LC". The height of the lateral canal is indicated by dots on the right part of the display section 7 (six dots in FIG. 10). The angle (the detected opening direction of the lateral canal) is indicated by the value in the top left of the display section 7. A resolution may be set at 10 degrees, for example. The approximate angle is indicated by ten bars forming a circle in the top of the display section 7.

By rotating the electrode 10' for direction detection arranged at the lateral canal position, the direction of the marking 10e at the time when the measured current In flowing between the electrode 10' and the buccal cavity electrode 11 becomes maximum can be checked as the lateral canal direction.

If the opening 10c provided in the insulating film 10b is small, the opening direction of the lateral canal can be detected with greater sensitivity; on the other hand, the accurate arrangement of the electrode 10' at the lateral canal position is required. If the opening 10c is large, although the detection sensitivity is sacrificed, the accuracy of arranging the electrode 10' at the lateral canal position will be decreased. The shape of the opening 10c may be circle or non-circle, as long as detection sensitivity is secured. The tip of the electrode 10' needs to be insulated in order to obtain waveforms of the measured currents; for example, an insulating coating may be applied at 1 mm from the tip up to 5 mm (preferably 2 mm), and from 2 mm to 5 mm (preferably 3 mm) of the electrode 10' above the insulating coating may be an opening. An opening of the electrode 10' may be up to above 3 mm. An electrode 10' with an opening which is formed by cutting off a part of the insulating coating after applying the insulating coating may be used. The insulating film may be formed by oxidizing the surface of a conductive metal to form an oxidized film.

By reducing the width of the opening 10c to make the opening 10c rectangular in a vertical direction, it is possible to make it easier to set the electrode 10' for direction detection at the lateral canal position without sacrificing the sensitivity in detecting the opening direction of the lateral canal.

Figure 9D:
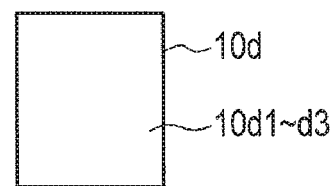
Figure 9D:
Figure 9B:
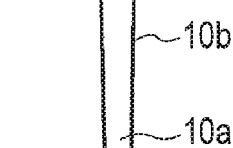
Figure 9C:
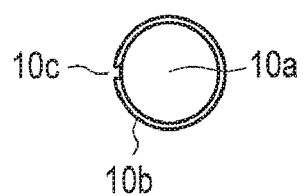

As shown in FIG. 9D, the outer surface of the opening 10c can be made even and smooth so that the opening 10c does not get caught easily on the inner wall of the root canal when inserting and rotating the electrode 10' in the root canal.

The above-described procedure for checking the lateral canal direction can be automated. The automation can be realized by providing, in the handle 10d, a rotation mechanism 10d1 for rotating the electrode 10', a detection mechanism 10d2 for detecting measured currents, and a detection mechanism 10d3 for detecting a rotation angle which exhibits a maximum measured current, for example.

Next, a method of detecting a position and an opening direction of the lateral canal using the lateral canal detection apparatus 100a shown in FIG. 1 is described. The method according to the first embodiment to be explained herein comprises detecting a lateral canal position and detecting an opening direction of the lateral canal.

The lateral canal position detection is described below. Different types of signals Pn used for measurement are alternately applied between the electrode 10 for position detection to be inserted into the root canal and the buccal cavity electrode 11 disposed on an inner surface of the buccal cavity. While applying the different types of signals Pn, the electrode 10 for position detection is inserted into the root canal, and first measured signals (In, Vn, or Vdc) each corresponding to the signals Pn used for measurement are detected at respective insertion positions of the electrode in the root canal. An electrode having a pin-shaped conductive metal portion is used as the electrode 10 for position detection, for example. Voltages at the above-mentioned frequencies, for example, are applied from the power source 1 as the signals Pn used for measurement. Each of the first measured signals are detected by the detection section 25. The first measured signal values detected by the detection section 25 are compared with the plurality of model tooth root apex position measurement data groups by the root apex position detection mechanism 12a. The root apex position detection mechanism 12a outputs the root apex position based on the result of comparison. The above-described data groups are used herein as a plurality of model tooth root apex position measurement data groups, and they are stored in advance.

Next, the first measured signal values are compared with the plurality of model tooth position measurement data groups by the electrode position detection mechanism 12b. As a result of the comparison, the electrode position detection mechanism 12b outputs an indication value indicating a distance from a root apex position indicated by a model tooth position measurement data group in a predetermined relationship to the distal end of the electrode for position detection. The above-described data groups are used herein as a plurality of model tooth position measurement data groups, and they are stored in advance. The first measured signal values and the indication value, which are output from the electrode position detection mechanism 12b and which change as the electrode 10 for position detection is inserted into the root canal, when the fluctuation waveform of the indication value shows an apex in a convex shape, are stored in the second storage section 14 by the lateral canal and lateral canal position detection mechanism 12c.

Consequently, the lateral canal position detection is once again performed, and the lateral canal and lateral canal position detection mechanism 12c compares the second-time measured signal values and the indication value with the stored first-time measured signal values and the stored indication values, respectively. When, as a result of the comparison, at least two of the signals and values match or fall within a predetermined error range, the lateral canal and lateral canal position detection mechanism 12c stops the electrode for position detection and measures the position of the distal end of the electrode to output as the lateral canal position.

The lateral canal direction detection is described below. After the above-described lateral canal position detection, the electrode 10 for position detection is replaced with the electrode 10' for direction detection, and different signals Pn used for measurement are alternately applied between the electrode 10' and the buccal cavity electrode 11. While applying the different signals Pn used for measurement, the distal end of the electrode for direction detection is rotated in the long axis rotation direction at the lateral canal position detected by the above-described lateral canal position detection, and the second measured signals corresponding to the signals used for measurement are detected. Voltages at the above-mentioned frequencies, for example, are applied from the power source 1 as the signals Pn used for measurement. The above-described electrode is used as the electrode 10' for direction detection. Each of the second measured signals is detected by the detection section 25. The lateral canal direction detection mechanism 12d outputs, as an opening direction of the lateral canal, the direction of the opening of the electrode 10' for direction detection when the values of the second measured signals, which change as the electrode 10' is rotated at the lateral canal position, detected by the detection section 25 reach maximum.

The step of measuring the position of the distal end of the electrode 10 for position detection can include measuring a distance from the distal end of the electrode 10 to the stopper 10f after fixing the electrode 10 by bringing down the stopper 10f to the top of the subject tooth. If the apparatus shown in FIG. 1 is provided with a measurement mechanism, the measurement mechanism can perform this additional measurement.

The method described herein may be implemented by firmware or software, or a combination thereof, for example.

If the method is implemented by firmware or software, or a combination thereof, the functions of the present method may be recorded on a computer readable storage medium which acts as a program executed by a computer, which is firmware, or software, or a combination thereof.

Figure 11:
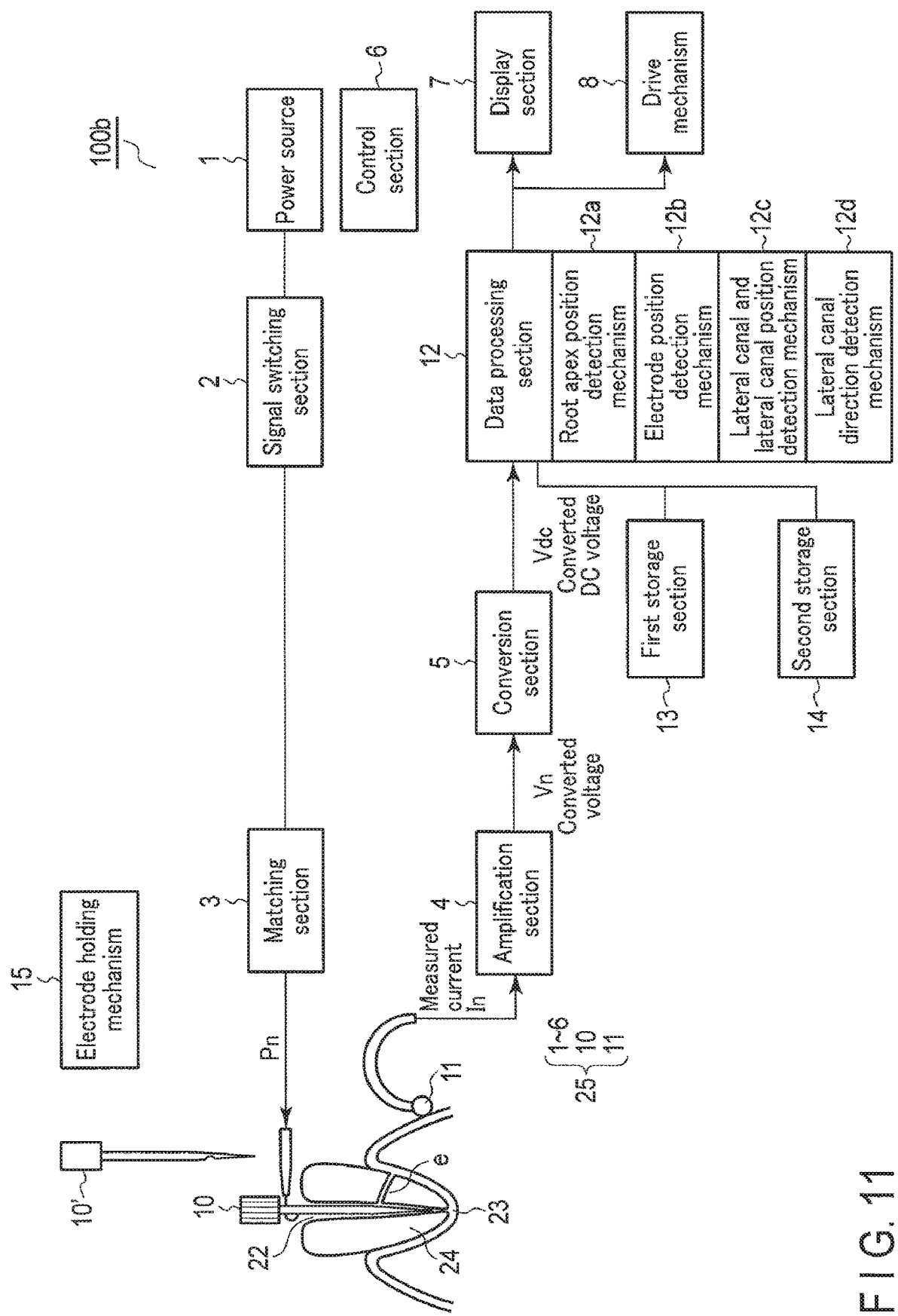
FIG. 11 is a block diagram showing a circuit of the lateral canal detection apparatus according to one embodiment of the present invention.

The lateral canal detection apparatus 100b of the second embodiment will be described with reference to FIG. 11. The apparatus shown in FIG. 11 is the same as the apparatus shown in FIG. 1, except for the electrode holding mechanism 15 for holding the electrode 10' for direction detection. The descriptions of the functions that are the same as those of the apparatus shown in FIG. 1 are omitted. In the following, the function of detecting an opening direction of a lateral canal using the electrode 10' for direction detection is described.

Figure 12:
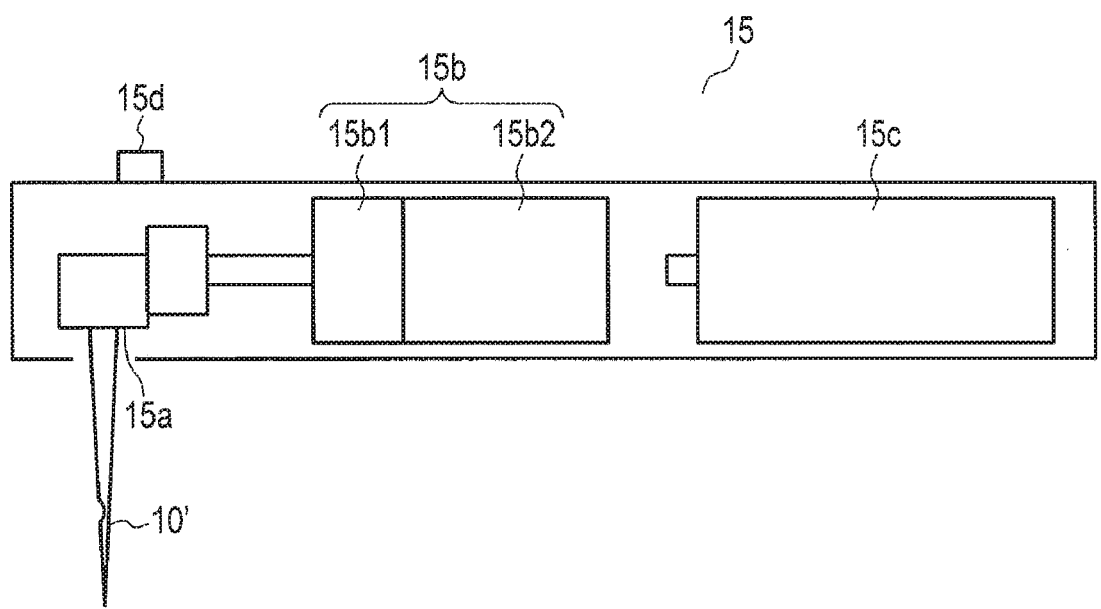
FIG. 12 is a sectional view of an electrode holding mechanism which holds the measurement electrode for direction detection according to one embodiment of the present invention.

The lateral canal detection apparatus 100b shown in FIG. 11 is provided with an electrode holding mechanism 15 for holding the electrode 10'. An example of the electrode holding mechanism 15 is shown in FIG. 12. The electrode holding mechanism 15 is provided with a holding section 15a which holds the electrode 10', and a rotation mechanism 15b which transmits rotation to the holding section 15a. By rotating the rotation mechanism 15a, the electrode 10' can be rotated in the long axis rotation direction. The electrode holding mechanism 15 can realize an ultra-low speed rotation to rotate the electrode 10' mechanically and smoothly for highly accurate measurement. Any mechanism can be adopted as the electrode holding mechanism 15, as long as it is capable of rotating the electrode 10' at a low speed mechanically and smoothly; such a mechanism is not limited to the electrode holding mechanism 15 shown in FIG. 12. The electrode holding mechanism 15 comprises a holding section 15a, a rotation mechanism 15b consisting of a gear 15b1 and a motor 15b2, a battery 15c, and a power switch 15d. Upon turning the power switch 15d ON, the motor 15b2 rotates the gear 15b1, and the electrode 10' for direction detection held by the holding section 15a is rotated.

The rotation mechanism 15b can be manufactured by using a gear as a motor so that the mechanism rotates in about one or two seconds.

The electrode 10' for direction detection is arranged at the lateral canal position detected by the same procedure as that in the first embodiment. The detection section 25 sequentially detects measured currents corresponding to the signals Pn between the electrode 10' and the buccal cavity electrode 11 during the process of rotating the electrode 10' in the long axis rotation direction at the detected lateral canal position. At this position, the power source 1 sequentially applies different types of signals Pn used for measurement between the electrode 10' for direction detection and the buccal cavity electrode 11 by switching between the signals, and the distal end of the electrode 10' is rotated in the long axis rotation direction in the root canal by rotating the rotation mechanism 15b by the electrode holding mechanism 15. The lateral canal direction detection mechanism 12d can detect the direction of the opening 10c of the electrode 10' for direction detection, as the opening direction of the lateral canal, at the time when each of the measured currents corresponding to respective measurement-used signals becomes maximum in correspondence to the rotation angle at which the electrode 10' is rotated at the detected lateral canal position by the electrode holding mechanism 15. Since mechanically smooth rotation at a low speed can be realized by the electrode holding mechanism 15, the opening direction of the lateral canal can be detected with higher accuracy.

Figure 13:
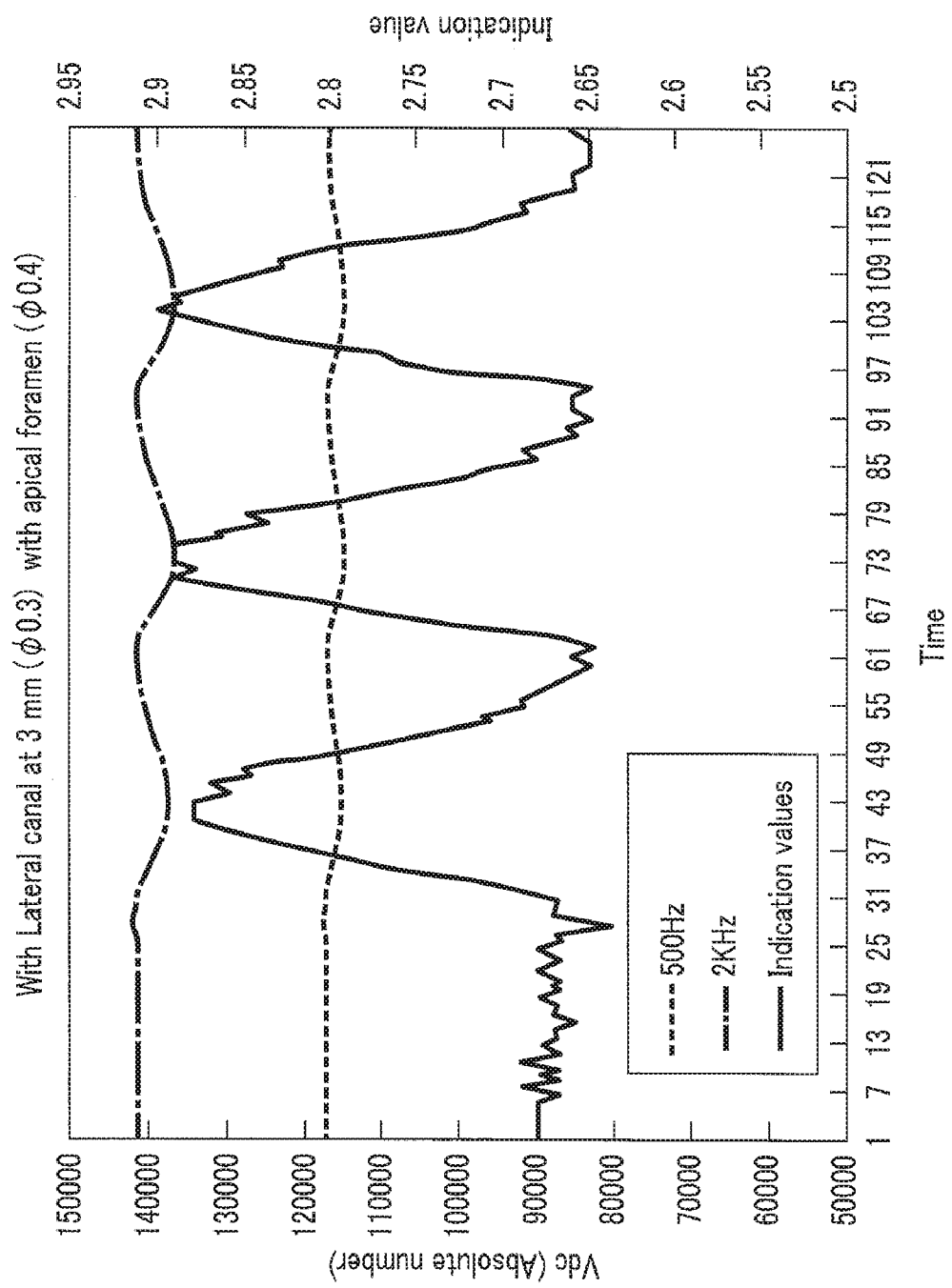
FIG. 13 is a diagram showing fluctuation waveforms of DC voltages obtained by converting measured currents when rotating the measurement electrode for direction detection in a root canal according to one embodiment of the present invention, and indication values indicating distances between the opening of the measurement electrode for direction detection and the lateral canal.

FIG. 13 is a graph showing a result of measurement when the electrode 10' for direction detection is rotated with respect to a subject tooth having a lateral canal, being held by the electrode holding mechanism 15 shown in FIG. 12 provided with an ultra low-speed motor. The horizontal axis denotes a data sampling time, and one unit of data sampling time is 60 ms, and the graph shows the result of data sampling for a duration of approximately 7.5 seconds. The vertical axis denotes DC voltage values obtained by converting a plurality of measured currents which are sequentially detected between the electrode 10' and the buccal cavity electrode 11 corresponding to the signals Pn used for measurement of 500 Hz and 2 kHz, and an indication value indicating a distance between the opening of the electrode 10' and the lateral canal calculated based on the DC voltage. The measured signals each corresponding to the measurement-used signals may be expressed by any of In, Vn, and Vdc. FIG. 13 shows a status where the electrode 10' for direction detection is stopped between one second and thirty seconds on the time axis, and the rotation of the motor starts from around thirty seconds on the time axis. When the indication value is minimum, the DC voltage value is maximum; thus, it can be determined that the opening 10c of the electrode 10' is located at the lateral canal position. On the other hand, when the indication value is maximum, the DC voltage value is minimum; thus, it can be determined that the opening 10c of the electrode 10' is located opposite to the lateral canal position. The indication value when the electrode 10' is stopped and the minimum indication value when the electrode 10' is rotated are approximately equal. Since mechanically smooth rotation at a low speed can be realized by the electrode holding mechanism 15, the fluctuation waveform of the indication value as shown in FIG. 13 can be obtained. FIG. 13 is a graph of the indication value indicated by a certain model tooth position measurement data group having a predetermined relationship, as a result of comparing a plurality of model tooth position measurement data groups, based on the DC voltages Vdc obtained by converting the measured In. If an indication value indicating a distance between the opening of the electrode 10' for direction detection and the lateral canal is obtained, a plurality of model tooth position measurement data groups do not have to be used. The angle of the lateral canal can be determined by comparing an indication value when the electrode 10' for direction detection is stopped with data corresponding to one rotation of the motor. In other words, the opening direction of the lateral canal can be calculated based on the indication value indicating a distance between the opening of the electrode 10' and the lateral canal, which is based on the measured signal values (In, Vn, or Vdc) respectively corresponding to the measurement-used signals. Thus, the opening direction of the lateral canal can be detected with higher accuracy. Furthermore, the opening direction of the lateral canal can be calculated based on the indication value before rotating the electrode 10' for direction detection, and minimum and maximum values of the indication value. If the opening position direction of the electrode 10' is fixed when inserting the electrode 10' into a tooth, the angle which indicates the opening direction of the lateral canal can be calculated. In this graph, the indication valve when the electrode 10' is stopped and the minimum value of the indication value when the electrode 10' is rotated are approximately the same; thus, it can be determined from the graph that the lateral canal is located at the angle of zero degrees.

Figure 14A:
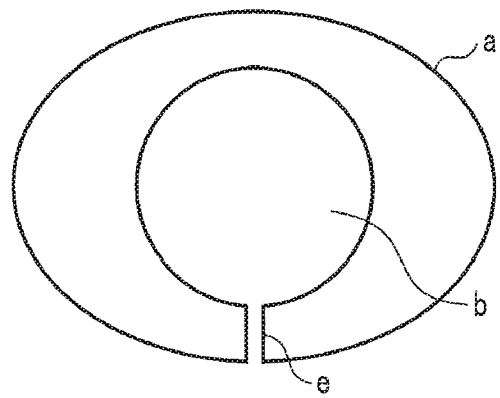
FIGS. 14A and B are diagrams to explain the state when the measurement electrode for direction detection according to one embodiment of the present invention is rotated in a root canal.

FIGS. 14A and B are sectional views of the subject tooth and the electrode 10' for direction detection. In FIGS. 14A and B, the subject tooth and the electrode 10' are separately drawn; in reality, the electrode 10' is inserted into the root canal of the subject tooth. In the following, the state when the electrode 10' for direction detection is rotated inside the root canal is described.

Figure 14B:
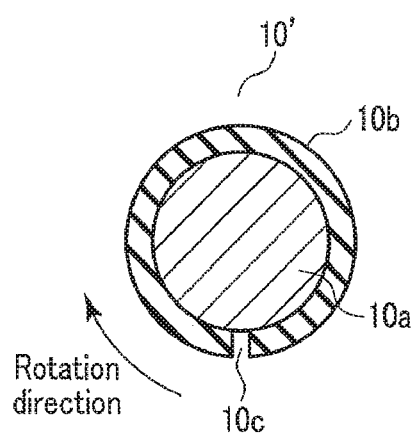

FIGS. 14A and B show that the opening c of the electrode 10' and the lateral canal "e" are in approximately the same direction; thus, it can be determined that a large current can flow. If the electrode 10' is rotated in the rotation direction shown in FIG. 14B, the lateral canal and the opening "c" of the electrode 10' are moved away from one another; thus, the current will gradually be less. If the opening "c" of the electrode 10' is opposite to the lateral canal, the current becomes minimum and then gradually becomes greater. If the position of the opening "c" is fixed in advance (e.g., a position on the cheek side is adjusted to the marking 10e of the electrode 10' in FIGS. 14A and B) when inserting the electrode 10', the angle indicating a direction of the lateral canal can be calculated as long as an indication value when the electrode 10' is in a stopped state, an indication value when a current becomes maximum, and an indication value when a current becomes minimum are known.

The display section 7 can display, selectively or entirely, the detected lateral canal direction and display data for displaying fluctuation waveforms of the plurality of measured signals (In, Vn, or Vdc) and the indication values.

Next, a method of detecting a lateral canal position and an opening direction of the lateral canal in the lateral canal detection apparatus 100b shown in FIG. 11 is described. In the descriptions of the method according to the second embodiment, the descriptions of the steps that are the same as those of the method according to the first embodiment are omitted.

In the method for detecting a lateral canal position and an opening direction of the lateral canal according to the second embodiment, a step of rotating the electrode 10' for direction detection in a long axis rotation direction by rotating the rotation mechanism 15b by the electrode holding mechanism 15 that comprises the holding section 15a which holds the electrode 10' and the rotating mechanism 15b which transmits rotation to the holding section 15a, is added to the lateral canal direction detection of the method described in the first embodiment. For example, if the electrode 10' is provided with the stopper 10f for fixing the electrode 10' to a subject tooth, the following two steps can be added prior to that of the above-described step. One is a step of setting the position of the stopper 10f of the electrode 10' based on a detected lateral canal position. The other is a step of inserting the electrode 10' into the root canal and arranging the direction detection electrode 10' at a position where the stopper 10f of the electrode 10' touches the top of a subject tooth.

With the method of detecting a position of a lateral canal and an opening direction thereof according to the second embodiment, the opening direction of the lateral canal can be calculated based on the indication value indicating a distance between the opening of the electrode 10' for direction detection and the lateral canal. Furthermore, the opening direction of the lateral canal can be calculated based on the indication value before rotating the electrode 10' for direction detection, and minimum and maximum values of the indication value.

The method described herein may be implemented by firmware or software, or a combination thereof, for example. If the method is implemented by firmware or software, or a combination thereof, the functions of the present method may be recorded on a computer readable storage medium which acts as a program executed by a computer, which is firmware, software, or a combination thereof.

Figure 15:
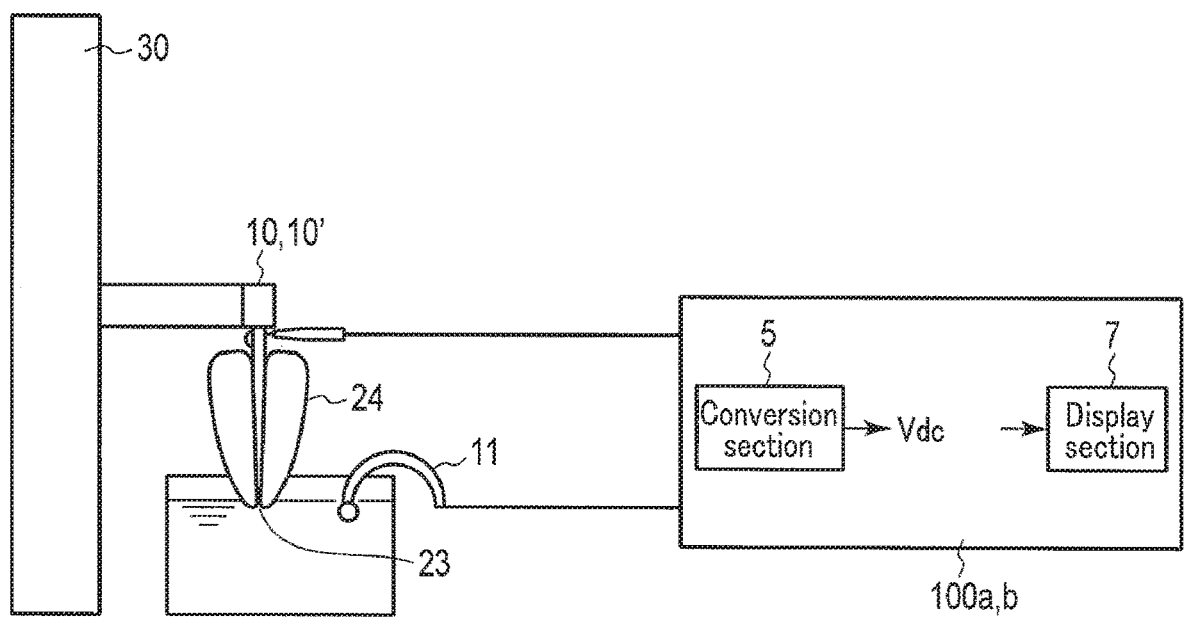
FIG. 15 is a diagram explaining an experiment circumstance when data shown in FIGS. 3-6 and 13 is measured.
Figure 16:
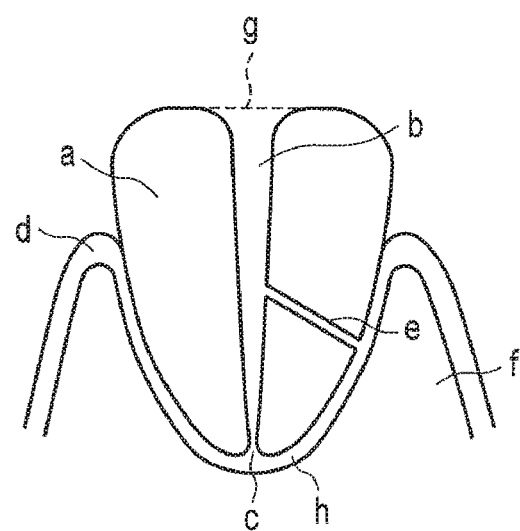
FIG. 16 is a sectional view of a tooth having a lateral canal and an apical foramen.

The circumstances of when the data shown in FIGS. 3-6 and 13 were measured is explained with respect to FIG. 15. FIG. 15 shows a measurement circuit which was used for the measurement. The lateral canal detection apparatus 100a (FIG. 1) and 100b (FIG. 11) applies a square wave voltage of 50 mV at each frequency of 500 Hz, 1 kHz, 2 kHz, 4 kHz, and 8 kHz to the electrode 10 for position detection and the electrode 10' for direction detection. A current In output from the buccal cavity electrode 11 is converted into a DC voltage Vdc, and the Vdc is stored and displayed on the display section 7. The subject tooth 24 was stood in physiological saline, and the electrode 10 for position direction was inserted into the root canal, and the memory of the height gauge 30 was determined to be 0 at the root apex position. The distance for which the electrode 10 is inserted from the root canal entrance can be read by the height gauge and can be stored. The measured current In output from the buccal cavity electrode was converted into a DC voltage Vdc at the conversion section 5, stored, and displayed on the display section 7. A lateral canal hole was formed in the subject tooth using a drill. The root apex hole and the lateral canal hole were filled with wax as needed, when measurement was conducted.

As described above, according to one embodiment of the present invention, it is possible to detect a position of a lateral canal with higher accuracy. Further according to the present invention, it is possible to detect an opening direction of a lateral canal with higher accuracy.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A method of detecting a position of a lateral canal extending from a root canal to a periodontal space using a lateral canal detection apparatus including a detection section and a data processing section, the detection section comprising an electrode for position detection and a buccal cavity electrode for disposition on an inner surface of a buccal cavity, the data processing section comprising an electrode position detection mechanism and a lateral canal and lateral canal position detection mechanism, the method comprising:

performing, by the data processing section, a first detection within a first range in a depth direction in the root canal of a tooth; and performing, by the data processing section, a second detection within a second range narrower than the first range in the depth direction in the root canal after the first detection, wherein the first range is a range from the top of the tooth to a root apex, and the second range overlaps at least in part of the first range, and performing the first detection comprises:

while the electrode for position detection is being inserted in the depth direction into the root canal, at a plurality of depth positions within the first range, obtaining, by the detection section, a first value obtained when a first signal is applied between the electrode for position detection and the buccal cavity electrode;

obtaining, by the detection section, a second value obtained when a second signal is applied between the electrode for position detection and the buccal cavity electrode; and selecting, by the electrode position detection mechanism, a first one of sets from a first data group based on the first value and the second value, the first data group including a plurality of the sets, each of the sets including a third value obtained when the first signal is applied, a fourth value obtained when the second signal is applied, and a first indication value at each of a plurality of positions in the root canal in each of a plurality of model teeth, and obtaining, by the electrode position detection mechanism, the first indication value in the selected first one of the sets as a second indication value, wherein the first indication value indicates a distance from the root apex position to a distal end of the electrode for position detection; and after the electrode for position detection reaches the root apex position, storing, by the lateral canal and lateral canal position detection mechanism, the first value, the second value and the second indication value at the time when a fluctuation of a plurality of the second indication values obtained within the first range shows an apex in a convex shape as a first reference value, a second reference value and a third reference value, respectively;

wherein performing the second detection comprises:
while the electrode for position detection is being inserted in the depth direction into the root canal, at a plurality of depth positions within the second range, obtaining, by the detection section, a fifth value obtained when the first signal is applied between the electrode for position detection and the buccal cavity electrode;

obtaining, by the detection section, a sixth value obtained when the second signal is applied between the electrode for position detection and the buccal cavity electrode;

selecting, by the electrode position detection mechanism, a second one of the sets from the first data group based on the fifth value and the sixth value, and obtaining, by the electrode position detection mechanism, the first indication value in the selected second one of the sets as a third indication value; and comparing, by the lateral canal and lateral canal position detection mechanism, the fifth value with the first reference value, the sixth value with the second reference value, and the third indication value with the third reference value, respectively; and if compared both values correspond or a difference between compared both values falls within a predetermined error range in at least two of the comparison of the fifth value with the first reference value, the comparison of the sixth value with the second reference value, and the comparison of the third indication value with the third reference value, informing, by the lateral canal and lateral canal position detection mechanism, an operator by displaying data output from the data processing section; stopping, by the lateral canal and lateral canal position detection mechanism, the electrode for position detection; and measuring, by the lateral canal and lateral canal position detection mechanism, a position of the distal end of the electrode for position detection; and outputting, by the lateral canal and lateral canal position detection mechanism, a result of the measurement as a position of the lateral canal.

2. The method according to claim 1, wherein the electrode for position detection comprises a stopper to fix the electrode for position detection to a subject tooth, wherein the measuring of the position of the distal end of the electrode for position detection comprises measuring a distance from the distal end of the electrode for position detection to the stopper after bringing down the stopper to the top of the subject tooth and fixing the electrode thereto.

3. The method according to claim 1, wherein the detection section further comprises an electrode for direction detection, and the data processing section further comprises a lateral canal direction detection mechanism, the method further comprises performing, by the data processing section, a third detection after the second detection, and wherein performing the third detection comprises:
while a distal end of the electrode for direction detection is being rotated in the long axis rotation direction at the position of the lateral canal obtained in the second detection with an electrode holding mechanism comprising a rotation mechanism, obtaining, by the detection section, a seventh value obtained when a third signal is applied between the electrode for direction detection and the buccal cavity electrode; and obtaining, by the detection section, an eighth value obtained when a fourth signal is applied between the electrode for direction detection and the buccal cavity electrode; and outputting, by the lateral canal direction detection mechanism, as an opening direction of the lateral canal, a direction of an opening of the electrode for direction detection at the time when the seventh value and the eighth value reaches maximum, wherein the electrode for direction detection has a conductive metal portion, and an insulating film coating the surface of the conductive metal portion, and the insulating film has the opening to expose the conductive metal portion in the long axis direction of a distal end portion of the conductive metal portion.

4. The method according to claim 3, further comprising, by the electrode holding mechanism provided with a holding section which holds the electrode for direction detection and the rotation mechanism which transmits rotation to the holding section, rotating the distal end of the electrode for direction detection at the detected lateral position in the long axis rotation direction by rotating the rotation mechanism.

5. The method according to claim 4, wherein the opening direction of the lateral canal is calculated based on a fourth indication value which indicates a distance between the opening of the electrode for direction detection and the lateral canal, the fourth indication value being based on the seventh value and the eighth value.

6. The method according to claim 5, wherein the electrode for position detection comprises a stopper to fix the electrode for position detection to a subject tooth, wherein the measuring of the position of the distal end of the electrode for position detection comprises measuring a distance from the distal end of the electrode for position detection to the stopper after bringing down the stopper to the top of the subject tooth and fixing the electrode thereto, wherein the electrode for direction detection comprises a stopper to fix the electrode for direction detection to a subject tooth, the method comprising:
setting the position of the stopper of the electrode for direction detection based on the detected lateral canal position; and
arranging the electrode for direction detection at a position where the stopper of the electrode for direction detection is in contact with the top of the subject tooth.

7. The method according to claim 4, wherein the electrode for position detection comprises a stopper to fix the electrode for position detection to a subject tooth, wherein the measuring of the position of the distal end of the electrode for position detection comprises measuring a distance from the distal end of the electrode for position detection to the stopper after bringing down the stopper to the top of the subject tooth and fixing the electrode thereto, wherein the electrode for direction detection comprises a stopper to fix the electrode for direction detection to a subject tooth, the method comprising:
setting the position of the stopper of the electrode for direction detection based on the detected lateral canal position; and
arranging the electrode for direction detection at a position where the stopper of the electrode for direction detection is in contact with the top of the subject tooth.

8. The method according to claim 1, wherein the data processing section further comprises a root apex position detection mechanism, performing the first detection further comprises:
obtaining, by the root apex position detection mechanism, the root apex position from a second data group based on the first value and the second value, the second data group including a plurality of sets, each of the sets including a ninth value obtained when the first signal is applied, and a tenth value obtained when the second signal is applied at the root apex position in each of a plurality of model teeth.

9. An apparatus for detecting a position of a lateral canal extending from a root canal to a periodontal space, the apparatus comprising:
a detection section which comprises an electrode for position detection and a buccal cavity electrode for disposition on an inner surface of a buccal cavity;
a power source which applies a first signal and a second signal between the electrode for position detection and the buccal cavity electrode;
a first storage section which stores a first data group;
a second storage section; and
a data processing section which comprises an electrode position detection mechanism and a lateral canal and lateral canal position detection mechanism, wherein:
the data processing section is configured to perform
a first detection within a first range in a depth direction in the root canal of a tooth; and
a second detection within a second range narrower than the first range in the depth direction in the root canal after the first detection,
wherein the first range is a range from the top of the tooth to a root apex, and the second range overlaps at least in part of the first range, and performing the first detection comprises:
while the electrode for position detection is being inserted in the depth direction into the root canal, at a plurality of depth positions within the first range,
obtaining, by the detection section, a first value obtained when the first signal is applied between the electrode for position detection and the buccal cavity electrode;
obtaining, by the detection section, a second value obtained when the second signal is applied between the electrode for position detection and the buccal cavity electrode; and
selecting, by the electrode position detection mechanism, a first one of sets from the first data group based on the first value and the second value, the first data group including a plurality of the sets, each of the sets including a third value obtained when the first signal is applied, a fourth value obtained when the second signal is applied, and a first indication value at each of a plurality of positions in the root canal in each of a plurality of model teeth, and obtaining, by the electrode position detection mechanism, the first indication value in the selected first one of the sets as a second indication value, wherein the first indication value indicates a distance from the root apex position to a distal end of the electrode for position detection; and
after the electrode for position detection reaches the root apex position, storing, by the lateral canal and lateral canal position detection mechanism, in the second storage section, the first value, the second value and the second indication value at the time when a fluctuation of a plurality of the second indication values obtained within the first range shows an apex in a convex shape as a first reference value, a second reference value and a third reference value, respectively;
wherein performing the second detection comprises:
while the electrode for position detection is being inserted in the depth direction into the root canal, at a plurality of depth positions within the second range,
obtaining, by the detection section, a fifth value obtained when the first signal is applied between the electrode for position detection and the buccal cavity electrode;
obtaining, by the detection section, a sixth value obtained when the second signal is applied between the electrode for position detection and the buccal cavity electrode;
selecting, by the electrode position detection mechanism, a second one of the sets from the first data group based on the fifth value and the sixth value, and obtaining, by the electrode position detection mechanism, the first indication value in the selected second one of the sets as a third indication value; and
comparing, by the lateral canal and lateral canal position detection mechanism, the fifth value with the first reference value, the sixth value with the second reference value, and the third indication value with the third reference value, respectively; and
if compared both values correspond or a difference between compared both values falls within a predetermined error range in at least two of the comparison of the fifth value with the first reference value, the comparison of the sixth value with the second reference value, and the comparison of the third indication value with the third reference value, informing, by the lateral canal and lateral canal position detection mechanism, an operator by displaying data output from the data processing section; stopping, by the lateral canal and lateral canal position detection mechanism, the electrode for position detection; and measuring, by the lateral canal and lateral canal position detection mechanism, a position of the distal end of the electrode for position detection; and outputting, by the lateral canal and lateral canal position detection mechanism, a result of the measurement as a position of the lateral canal.

10. The apparatus according to claim 9, wherein the electrode for position detection comprises a stopper to fix the electrode for position detection to a subject tooth, and the apparatus comprises a measurement mechanism which measures a distance from a distal end of the electrode for position detection to the stopper after bringing down the stopper to the top of the subject tooth and fixing the electrode thereto.

11. The apparatus according to claim 9, further comprising a display section which displays, selectively or entirely, data output from the data processing section.

12. The apparatus according to claim 9, wherein the detection section further comprises an electrode for direction detection, the power source further applies a third signal and a fourth signal between the electrode for direction detection and the buccal cavity electrode, the data processing section further comprises a lateral canal direction detection mechanism, the data processing section further performs a third detection after the second detection, and
wherein performing the third detection comprises:
while a distal end of the electrode for direction detection is being rotated in the long axis rotation direction at the position of the lateral canal obtained in the second detection,
obtaining, by the detection section, a seventh value obtained when the third signal is applied between the electrode for direction detection and the buccal cavity electrode; and
obtaining, by the detection section, an eighth value obtained when the fourth signal is applied between the electrode for direction detection and the buccal cavity electrode; and
outputting, by the lateral canal direction detection mechanism, as an opening direction of the lateral canal, a direction of an opening of the electrode for direction detection at the time when the seventh value and the eighth value reaches maximum,
wherein the electrode for direction detection has a conductive metal portion, and an insulating film coating the surface of the conductive metal portion, and the insulating film has the opening to expose the conductive metal portion in the long axis direction of a distal end portion of the conductive metal portion.

13. The apparatus according to claim 12, further comprising an electrode holding mechanism comprising a holding section which holds the electrode for direction detection and a rotation mechanism which transmits rotation to the holding section,
wherein the lateral canal direction detection mechanism rotates the distal end of the electrode for direction detection at the detected lateral canal position in the long axis rotation direction by rotating the rotation mechanism by the electrode holding mechanism.

14. The apparatus according to claim 13, wherein the opening direction of the lateral canal is calculated based on a fourth indication value which indicates a distance between the opening of the electrode for direction detection and the lateral canal, the fourth indication value being based on the seventh value and the eighth value.

15. The apparatus according to claim 14, wherein the electrode for position detection is provided with a stopper to fix the electrode for position detection to a subject tooth, wherein the apparatus comprises a measurement mechanism which measures a distance from the distal end of the electrode for position detection to the stopper after bringing down the stopper to the top of the subject tooth and fixing the electrode thereto,
wherein the electrode for direction detection comprises a stopper to fix the electrode for direction detection to a subject tooth,
the apparatus comprising:
a setting mechanism for setting the position of the stopper of the electrode for direction detection based on the detected lateral canal position; and
an arrangement mechanism for arranging the electrode for position detection at a position where the stopper of the electrode for direction detection is in contact with the top of the subject tooth.

16. The apparatus according to claim 13, wherein the electrode for position detection is provided with a stopper to fix the electrode for position detection to a subject tooth, wherein the apparatus comprises a measurement mechanism which measures a distance from the distal end of the electrode for position detection to the stopper after bringing down the stopper to the top of the subject tooth and fixing the electrode thereto,
wherein the electrode for direction detection comprises a stopper to fix the electrode for direction detection to a subject tooth,
the apparatus comprising:
a setting mechanism for setting the position of the stopper of the electrode for direction detection based on the detected lateral canal position; and
an arrangement mechanism for arranging the electrode for position detection at a position where the stopper of the electrode for direction detection is in contact with the top of the subject tooth.

17. The apparatus according to claim 9, wherein the data processing section further comprises a root apex position detection mechanism, performing the first detection further comprises:
obtaining, by the root apex position detection mechanism, the root apex position from a second data group based on the first value and the second value, the second data group including a plurality of sets, each of the sets including a ninth value obtained when the first signal is applied, and a tenth value obtained when the second signal is applied at the root apex position in each of a plurality of model teeth.

* * * * *